(12) United States Patent
Takei

(10) Patent No.: US 9,185,312 B2
(45) Date of Patent: Nov. 10, 2015

(54) IMAGE PICKUP SYSTEM

(71) Applicant: OLYMPUS MEDICAL SYSTEMS CORP., Tokyo (JP)

(72) Inventor: Shunji Takei, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/590,300

(22) Filed: Jan. 6, 2015

(65) Prior Publication Data

US 2015/0116561 A1    Apr. 30, 2015

Related U.S. Application Data

(63) Continuation of application No. PCT/JP2014/059973, filed on Apr. 4, 2014.

(30) Foreign Application Priority Data

Sep. 4, 2013   (JP) .................................. 2013-183289

(51) Int. Cl.
*H04N 5/353*   (2011.01)
*H04N 5/235*   (2006.01)
*A61B 1/04*    (2006.01)
(Continued)

(52) U.S. Cl.
CPC .............. *H04N 5/3532* (2013.01); *A61B 1/00* (2013.01); *A61B 1/04* (2013.01); *A61B 1/06* (2013.01); *G02B 23/26* (2013.01); *G03B 7/091* (2013.01); *G03B 15/03* (2013.01); *G03B 15/05* (2013.01); *H04N 5/238* (2013.01); *H04N 5/2352* (2013.01); *H04N 5/2353* (2013.01); *H04N 5/2354* (2013.01); *H04N 5/378* (2013.01)

(58) Field of Classification Search
CPC ....... A61B 1/06; H04N 5/3532; H04N 5/238; H04N 5/2355; H04N 5/2354; H04N 5/2353; G03B 15/02; G03B 15/05; G02B 23/26
USPC ............................. 348/370, 65, 68, 296, 371
See application file for complete search history.

(56) References Cited

U.S. PATENT DOCUMENTS

| 5,667,474 A | 9/1997 | Nishimura |
| 2008/0232130 A1 | 9/2008 | Suda |

(Continued)

FOREIGN PATENT DOCUMENTS

| EP | 2 407 087 A2 | 1/2012 |
| EP | 2 407 088 A2 | 1/2012 |

(Continued)

*Primary Examiner* — Nhan T Tran
(74) *Attorney, Agent, or Firm* — Scully, Scott, Murphy & Presser, P.C.

(57) ABSTRACT

An image pickup system includes: an image sensor that performs a rolling-shutter image pickup operation; a generator; an adding section that adds image pickup signals from an image pickup signal in a predetermined frame to an image pickup signal in an Nth frame, with the predetermined frame being set as a first frame; a light source; a signal output section that outputs a signal representing either a timing of start of readout of a first line in the predetermined frame or a timing of completion of readout of a last line in a frame immediately before the predetermined frame; and a light source control section that starts light emission after an input of the signal and terminates light emission in a period after completion of readout of a first line in an N-1th frame until before a start of a first line in the Nth frame.

3 Claims, 15 Drawing Sheets

(51) Int. Cl.
　　*G03B 15/05*　　　(2006.01)
　　*A61B 1/00*　　　(2006.01)
　　*A61B 1/06*　　　(2006.01)
　　*G02B 23/26*　　　(2006.01)
　　*G03B 7/091*　　　(2006.01)
　　*G03B 15/03*　　　(2006.01)
　　*H04N 5/238*　　　(2006.01)
　　*H04N 5/378*　　　(2011.01)

(56)　　　　References Cited

U.S. PATENT DOCUMENTS

| | | |
|---|---|---|
| 2009/0147077 A1 | 6/2009 | Tani et al. |
| 2012/0016200 A1 | 1/2012 | Seto et al. |
| 2012/0016201 A1 | 1/2012 | Seto et al. |
| 2013/0201315 A1* | 8/2013 | Takei et al. .................. 348/77 |
| 2014/0014820 A1* | 1/2014 | Yabe et al. ................ 250/208.1 |
| 2014/0194686 A1* | 7/2014 | Murayama ................... 600/109 |
| 2014/0364690 A1* | 12/2014 | Seto .............................. 348/70 |

FOREIGN PATENT DOCUMENTS

| | | |
|---|---|---|
| JP | 07-246184 A | 9/1995 |
| JP | 2003-070721 A | 3/2003 |
| JP | 2008-229222 A | 10/2008 |
| JP | 2009-136447 A | 6/2009 |
| JP | 2010-262224 A | 11/2010 |
| JP | 2012-019982 A | 2/2012 |
| JP | 2012-019983 A | 2/2012 |

* cited by examiner

IMAGE PICKUP SYSTEM

CROSS REFERENCE TO RELATED APPLICATION

This application is a continuation application of PCT/JP2014/059973filed on Apr. 4, 2014 and claims benefit of Japanese Application No. 2013-183289 filed in Japan on Sep. 4, 2013, the entire contents of which are incorporated herein by this reference.

BACKGROUND OF THE INVENTION

1. Field of the Invention

The present invention relates to an image pickup system, and more particularly to an image pickup system that obtains an image of an object using a CMOS image sensor.

2. Description of the Related Art

Various techniques have been conventionally proposed for preferably picking up an image of an object using a CMOS image sensor (hereinafter, also referred to as a CMOS image pickup device).

Specifically, Japanese Patent Application Laid-Open Publication No. 2009-136447, for example, discloses an endoscope system configured to cause a light source to carry out pulse light emission in a predetermined period (non-readout period) within a period for one field determined by a field signal supplied to a CMOS image pickup device and cause the light source to stop pulse light emission in a period (readout period) other than the predetermined period within the period for one field. In other words, the Japanese Patent Application Laid-Open Publication No. 2009-136447 discloses a method for suppressing brightness unevenness of an image picked up with the CMOS image pickup device by controlling the light emission state of the light source while operating the CMOS image pickup device by using another method different from the common rolling-shutter method which does not include a non-readout period.

SUMMARY OF THE INVENTION

An image pickup system according to one aspect of the present invention includes: an image sensor configured to receive light from an object and perform an image pickup operation using a rolling-shutter method in which exposure and readout are performed in a predetermined time cycle; a generator configured to generate a driving signal for controlling the image sensor such that exposure and readout are performed in the image sensor in the predetermined time cycle; an adding section configured to add image pickup signals from an image pickup signal in a predetermined frame, which is read out from the image sensor, to an image pickup signal in an Nth frame (N is an integer equal to or larger than 2) with the predetermined frame being set as a first frame, and output the added image pickup signals; a light source configured to emit light for illuminating the object; a trigger signal output section configured to output a trigger signal which represents either a first timing at which readout of a first line in the predetermined frame is started in the image sensor or a second timing at which readout of a last line in a frame immediately before the predetermined frame has been completed in the image sensor; and a light source control section configured to perform control for starting light emission by the light source after an input of the trigger signal from the trigger signal output section and terminating light emission by the light source in a period after completion of readout of a first line in an N-1th frame, with the predetermined frame as a reference, until before a start of readout of a first line in the Nth frame.

DETAILED DESCRIPTION OF THE PREFERRED EMBODIMENTS

Hereinafter, embodiments of the present invention will be described with reference to drawings.

First Embodiment

Figure 1:
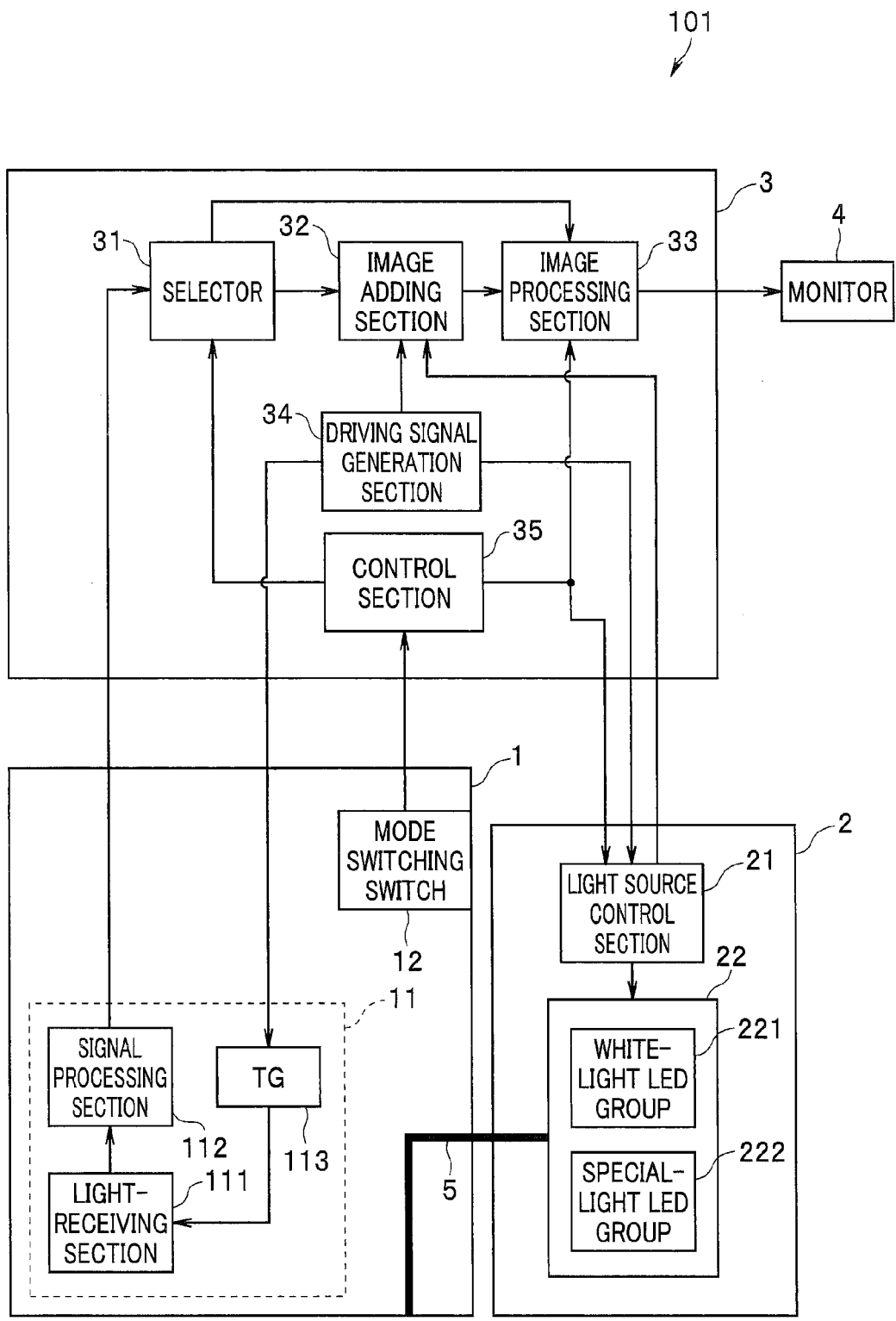
FIG. 1 illustrates a configuration of a main part of an image pickup system according to a first embodiment.

FIGS. 1 to 5 relate to the first embodiment of the present invention. FIG. 1 illustrates a configuration of a main part of an image pickup system according to the first embodiment.

As shown in FIG. 1, an image pickup system 101 includes: an endoscope 1 including a function as an image pickup apparatus that picks up an image of an object to obtain image data; a light source device 2 that emits illumination light for illuminating the object; a processor 3 that generates a video signal based on the image data obtained with the endoscope 1 and outputs the generated video signal; and a monitor 4 that displays an observation image corresponding to the video signal outputted from the processor 3, or other images.

The endoscope 1 includes an elongated-shaped insertion portion configured to be insertable into a body cavity, for example. In addition, the endoscope 1 includes a CMOS image sensor 11 provided at a distal end portion of the insertion portion, and a mode switching switch 12. Furthermore, inside the endoscope 1, a light guide 5 configured to be able to transmit the illumination light emitted from the light source device 2 and irradiate the object with the illumination light is inserted.

The CMOS image sensor 11 includes a light-receiving section 111, a signal processing section 112, and a timing generator (hereinafter, abbreviated as TG) 113.

The light-receiving section 111 is configured by including a plurality of pixels on respective lines from the first line L1 located at the uppermost position to the N-th line LN located at the lowermost position. In addition, the light-receiving section 111 is configured to perform an image pickup operation using a rolling-shutter method in which exposure and readout are performed in a predetermined time cycle based on an image pickup control signal outputted from the TG 113. In addition, the light-receiving section 111 is configured to be able to receive return light generated from the illumination light emitted to the object through the light guide 5, generate an electric signal corresponding to the received return light, and output the generated electric signal.

The signal processing section 112 is configured to generate image data by performing signal processing such as A/D conversion processing on the electric signal outputted from the light-receiving section 111 and output the generated image data to the processor 3.

The TG 113 is configured to generate an image pickup control signal to be described later based on a readout start signal outputted from the processor 3 and output the generated image pickup control signal.

The mode switching switch 12 is configured to, in response to an operation by a user, be able to give the processor 3 an instruction for setting the observation mode of the image pickup system 101 to either a white light observation mode or a special light observation mode.

The light source device 2 includes a light source control section 21, and an LED unit 22 including a white-light LED group 221 and a special-light LED group 222.

The light source control section 21 is configured to, when detecting that the observation mode of the image pickup system 101 is set to the white light observation mode, generate a light emission control signal for causing the respective LEDs which belong to the white-light LED group 221 to simultaneously and continuously emit light and causing the respective LEDs which belong to the special-light LED group 222 to stop light emission, and output the generated light emission control signal to the LED unit 22, based on a system control signal outputted from the processor 3. Furthermore, the light source control section 21 is configured to, when detecting that the observation mode of the image pickup system 101 is set to the special light observation mode, generate a light emission control signal for causing the respective LEDs which belong to the white-light LED group 221 to stop light emission and causing the respective LEDs which belong to the special-light LED group 222 to emit light and/or stop light emission at a timing corresponding to the readout start signal outputted from the processor 3, and output the generated light emission control signal to the LED unit 22 and the processor 3, based on the system control signal outputted from the processor 3.

The white-light LED group 221 includes one or more LEDs, for example, and emits white light by simultaneous light emission of the one or more LEDs.

The special-light LED group 222 includes a first LED that emits light in a first wavelength band (hereinafter, referred to as A light) and a second LED that emits light in a second wavelength band different from the first wavelength band (hereinafter, referred to as B light), for example, and is configured to emit light used for special light observation such as fluorescent light observation or narrow-band light observation.

That is, according to the above-described configuration, when the observation mode is set to the white light observation mode, white light emitted from the white-light LED group 221 is supplied as illumination light to the light guide 5 (endoscope 1). In addition, according to the above-described configuration, when the observation mode is set to the special light observation mode, light corresponding to the light emission state of the first and second LEDs in the special-light LED group 222 is supplied as illumination light to the light guide 5 (endoscope 1).

The processor 3 includes a selector 31, an image adding section 32, an image processing section 33, a driving signal generation section 34, and a control section 35.

The selector 31 is configured to, when detecting that the observation mode of the image pickup system 101 is set to the white light observation mode, output the image data outputted from the CMOS image sensor 11 to the image processing section 33, based on the system control signal outputted from the control section 35. In addition, the selector 31 is configured to, when detecting that the observation mode of the image pickup system 101 is set to the special light observation mode, output the image data outputted from the CMOS image sensor 11 to the image adding section 32, based on the system control signal outputted from the control section 35.

Figure 2:
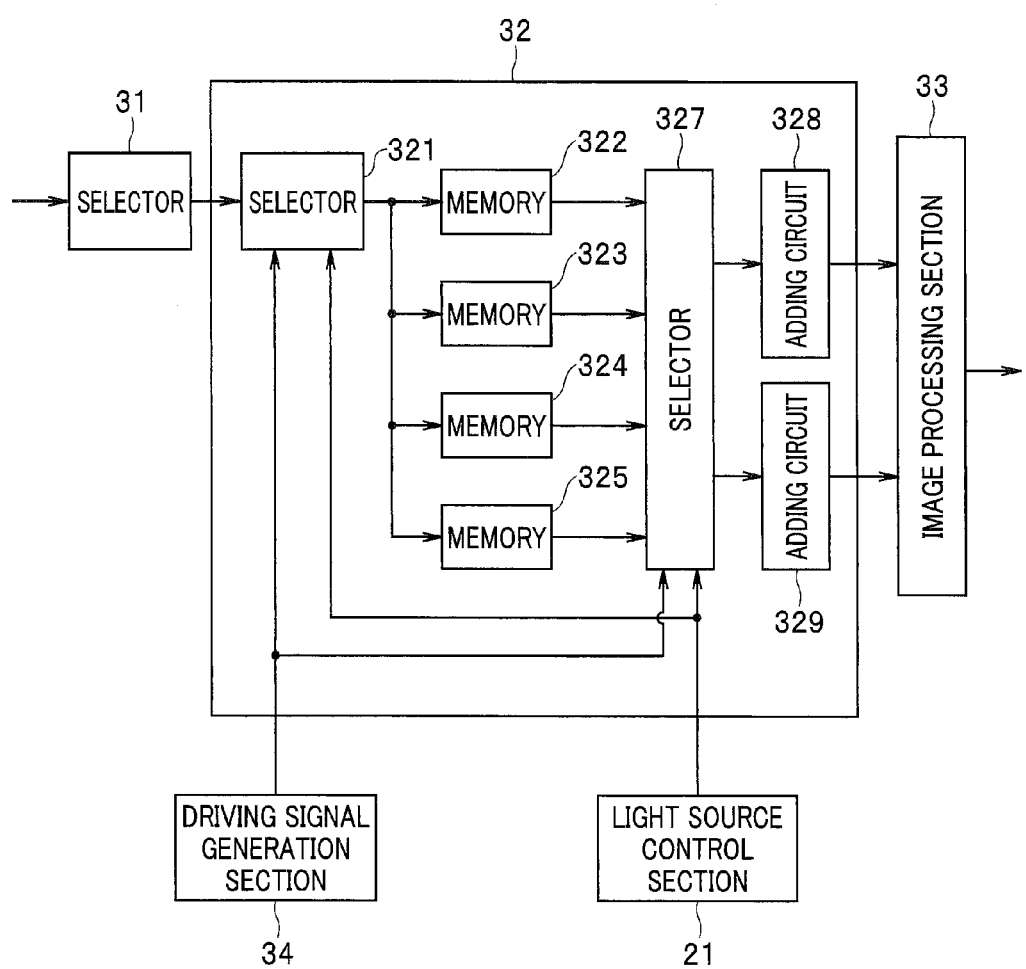
FIG. 2 is a block diagram showing an example of a specific configuration of an image adding section according to the first embodiment.

The image adding section 32 is configured to add and synthesize the image data outputted from the selector 31 when the observation mode is set to the special light observation mode and output the added and synthesized image data to the image processing section 33, based on the light emission control signal outputted from the light source control section 21 and the readout start signal outputted from the driving signal generation section 34. FIG. 2 is a block diagram showing an example of the specific configuration of the image adding section according to the first embodiment.

Specifically, as shown in FIG. 2, for example, the image adding section 32 includes a selector 321 provided at the subsequent stage of the selector 31, memories 322, 323, 324, and 325 provided in parallel at the subsequent stage of the selector 321, a selector 327 provided at the subsequent stage of the memories 322 to 325, and adding circuits 328, 329 provided in parallel at the subsequent stage of the selector 327.

The selector 321 is configured to output the image data inputted through the selector 31 to one of the memories 322 to 325, based on the light emission control signal outputted from the light source control section 21 and the readout start signal outputted from the driving signal generation section 34.

The memories 322 to 325 are configured of frame memories or the like, each of which is capable of storing image data, which is outputted from the selector 321, for one frame, for example.

The selector 327 is configured to simultaneously output the image data stored in the memories 322 to 325 to either the adding circuit 328 or the adding circuit 329, based on the light emission control signal outputted from the light source control section 21, and the readout start signal outputted from the driving signal generation section 34.

The adding circuits 328 and 329 are configured to perform adding processing on the image data for a plurality of frames which are simultaneously outputted from the selector 327, and output the image data subjected to the adding processing to the image processing section 33.

The image processing section 33 is configured to, based on the system control signal outputted from the control section 35, perform image processing corresponding to the white light observation mode on the image data outputted from the selector 31, to thereby generate a video signal and output the generated video signal to the monitor 4. In addition, the image processing section 33 is configured to, based on the system control signal outputted from the control section 35, perform image processing corresponding to the special light observation mode on the image data outputted from the image adding section 32, to thereby generate a video signal and output the generated video signal to the monitor 4.

The driving signal generation section 34 generates a readout start signal representing the timing for starting readout of the line L1 of the light-receiving section 111, once in each period T which corresponds to the frame rate related to image obtainment, and outputs the generated readout start signal to the CMOS image sensor 11, the light source control section 21, and the image adding section 32.

That is, with the image pickup system 101 according to the present embodiment, the driving signal generation section 34 includes a function as a trigger signal output section, and the readout start signal outputted from the driving signal generation section 34 has a function as a trigger signal.

The control section 35 is configured to generate a system control signal for setting the observation mode of the image pickup system 101 to either the white light observation mode or the special light observation mode based on the instruction given through the mode switching switch 12, and output the generated system control signal to the light source control section 21, the selector 31, and the image processing section 33.

Next, working of the image pickup system 101 having the above-described configuration will be described.

The user turns on power sources of the respective sections of the image pickup system 101, and thereafter operates the mode switching switch 12 to give an instruction for setting the observation mode of the image pickup system 101 to the white light observation mode.

The control section 35, based on the instruction given through the mode switching switch 12, generates a system control signal for setting the observation mode of the image pickup system 101 to the white light observation mode and outputs the generated system control signal to the light source control section 21, the selector 31, and the image processing section 33.

The driving signal generation section 34 generates the readout start signal representing the timing for starting the readout of the line L1 of the light-receiving section 111, once in each period T which corresponds to the frame rate related to image obtainment, and outputs the generated readout start signal to the TG 113, the light source control section 21, and the image adding section 32.

The TG 113, based on the readout start signal outputted once in each period T from the driving signal generation section 34, matches the exposure period of each line with the period T and generates an image pickup control signal for completing exposure of the line L1 and starting readout of the line L1 at a timing substantially immediately after the start of exposure of the line LN, to output the generated image pickup control signal to the light-receiving section 111.

On the other hand, the light source control section 21, when detecting that the observation mode of the image pickup system 101 is set to the white light observation mode based on the system control signal outputted from the control section 35, generates a light emission control signal for causing the respective LEDs which belong to the white-light LED group 221 to simultaneously and continuously emit light and causing the respective LEDs which belong to the special-light LED group 222 to stop light emission and outputs the generated light emission control signal to the LED unit 22. Then, in response to the output of such a light emission control signal, the white light emitted from the white-light LED group 221 is supplied to the light guide 5, and further, the object is illuminated with the white light applied through the light guide 5.

The light-receiving section 111 performs image pickup operation using the rolling-shutter method based on the image pickup control signal outputted from the TG 113, and thereby receives return light of the white light applied to the object, to generate an electric signal corresponding to the received return light and output the generated electric signal.

The signal processing section 112 generates image data by performing signal processing such as A/D conversion processing on the electric signal outputted from the light-receiving section 111, and outputs the generated image data to the selector 31.

The selector 31 operates so as to output the image data outputted from the signal processing section 112 to the image processing section 33, based on the system control signal outputted from the control section 35.

The image processing section 33, based on the system control signal outputted from the control section 35, performs image processing corresponding to the white light observation mode on the image data outputted from the selector 31, to thereby generate a video signal and output the generated video signal to the monitor 4. Specifically, the image processing section 33 performs processing such as white balance adjustment and gain adjustment on the image data outputted from the selector 31, for example, to thereby generate a video signal and output the generated video signal to the monitor 4.

On the other hand, the user operates the insertion portion of the endoscope 1 while checking the observation image displayed on the monitor 4 in the white light observation mode, and places the distal end portion of the insertion portion at a position where an image of a desired object in the body cavity can be picked up. The user then operates the mode switching switch 12 in the state where the distal end portion of the insertion portion is arranged as described above, to thereby give an instruction for setting the observation mode of the image pickup system 101 to the special light observation mode.

The control section 35, based on the instruction given through the mode switching switch 12, generates a system control signal for setting the observation mode of the image pickup system 101 to the special light observation mode and outputs the generated system control signal to the light source control section 21, the selector 31, and the image processing section 33.

Figure 3:
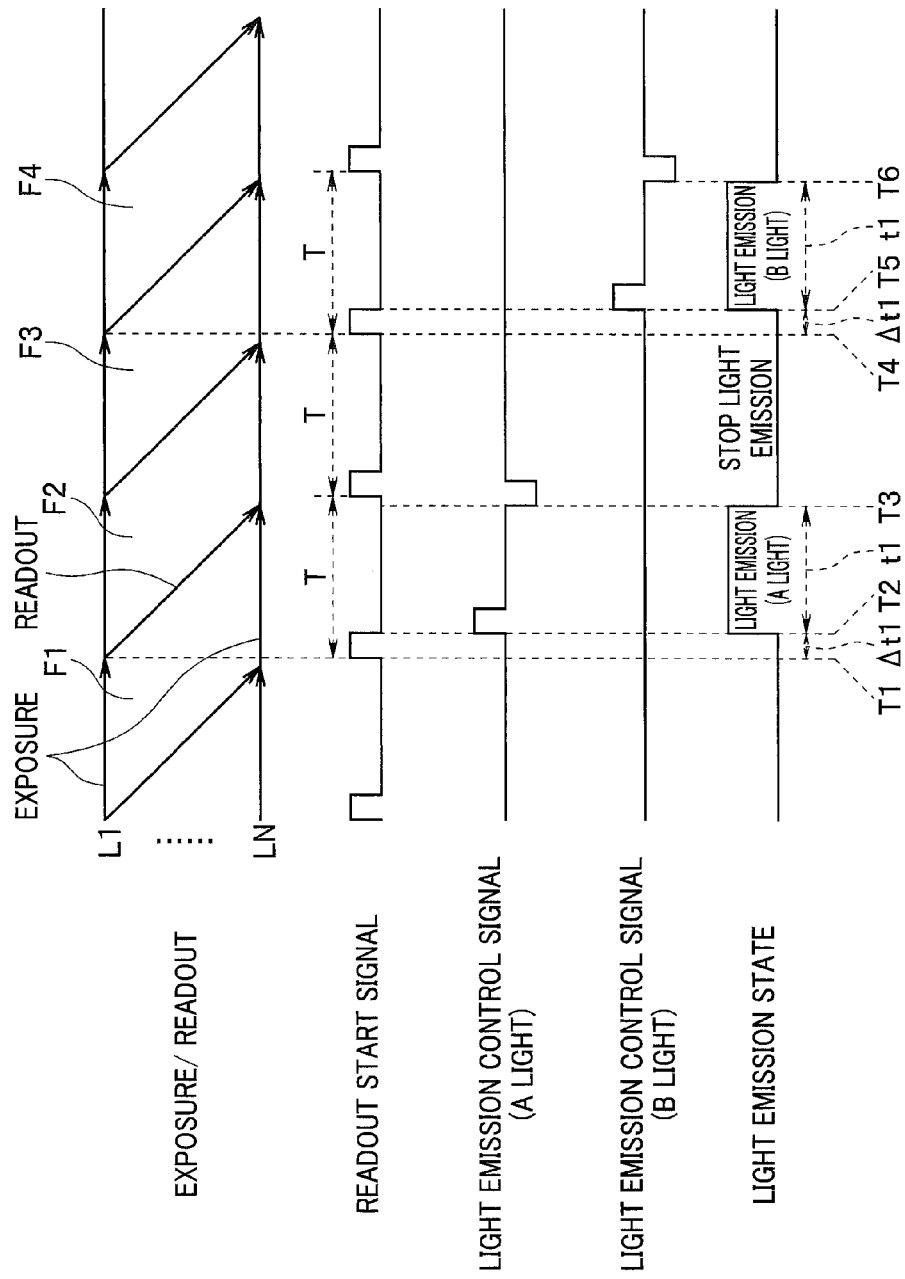
FIG. 3 illustrates an operation performed in the image pickup system according to the first embodiment.

Now, description will be made on the specific operation performed when the image pickup system 101 is set to the special light observation mode. FIG. 3 illustrates an operation performed in the image pickup system according to the first embodiment. Note that, hereinafter description will be made supposing that the readout of the line L1 located at the uppermost position of the light-receiving section 111 is performed first in one frame and the readout of the line LN located at the lowermost position of the light-receiving section 111 is performed last in the same one frame.

The TG 113, based on the readout start signal outputted once in each period T from the driving signal generation section 34, generates an image pickup control signal for completing exposure of the line L1 in a frame F1 and starting readout of the line L1 in the frame F1 at a time T1 corresponding to a timing substantially immediately after the start of the exposure of the line F11 in the frame F1, and outputs the generated image pickup control signal to the light-receiving section 111.

The light source control section 21 generates a light emission control signal for starting emission of the A light by the first LED in the special-light LED group 222 at a time T2 corresponding to a timing after a delay period Δt1 has elapsed from the time T1 at which the readout start signal was inputted from the driving signal generation section 34, and for terminating the emission of the A light by the first LED in the special-light LED group 222 at a time T3 corresponding to a timing after a light emission period t1 has elapsed from the time T2, and outputs the generated light emission control signal to the LED unit 22 and the image adding section 32A.

The light source control section 21, when generating the above-described light emission control signal, sets the light emission period t1 so as to include the time T3 in the period after the readout of the line L1 of the light-receiving section 111 has been completed for the frame F1 until before the readout of the line L1 is started for a frame F2 (for example, immediately before the readout of the line L1 is started for the frame F2). In addition, when generating the above-described light emission control signal, the light source control section 21 sets the delay period Δt1 such that the relation of Δt1<T−t1 is established, that is, the delay period Δt1 is smaller than the difference between the exposure period T of the line L1 in the frame F1 and the light emission period t1 of the first LED.

In response to the output of the above-described light emission control signal, in the light emission period t1 bridging over two frames, i.e., the frames F1 and F2, the A light emitted from (the first LED in) the special-light LED group 222 is supplied to the light guide 5, and further, the object is illuminated with the A light applied through the light guide 5.

The light-receiving section 111 performs image pickup operation using the rolling-shutter method based on the image pickup control signal outputted from the TG 113, to thereby receive the return light of the A light applied to the object in the light emission period t1, and generates an electric signal corresponding to the received return light, to output the generated electric signal.

The signal processing section 112 performs signal processing such as A/D conversion processing on the electric signal outputted from the light-receiving section 111, to sequentially generate image data for the two frames F1 and F2 and output the generated image data for the two frames to the selector 31.

The selector 31 operates so as to output the image data outputted from the signal processing section 112 to the image adding section 32A, based on the system control signal outputted from the control section 35.

The selector 321, based on the light emission control signal outputted from the light source control section 21 and the readout start signal outputted from the driving signal generation section 34, recognizes the image data inputted first after the start of the emission of the A light by the first LED in the special-light LED group 222, as the image data for the frame F1, and causes the memory 322 to store the image data for the frame F1. In addition, based on the light emission control signal outputted from the light source control section 21 and the readout start signal outputted from the driving signal generation section 34, the selector 321 recognizes the image data inputted secondly after the start of the emission of the A light by the first LED in the special-light LED group 222, as the image data for the frame F2, and causes the memory 323 to store the image data for the frame F2.

Based on the light emission control signal outputted from the light source control section 21 and the readout start signal outputted from the driving signal generation section 34, when the selector 327 detects that the image data for the frame F1 obtained following the emission of the A light is stored in the memory 322 and the image data for the frame F2 obtained following the emission of the A light is stored in the memory 323, the selector 327 simultaneously outputs the image data for the frames F1 and F2 to the adding circuit 328.

The adding circuit 328 performs adding processing on the image data for the frames F1 and F2 which are simultaneously outputted from the selector 327, and outputs the image data subjected to the adding processing to the image processing section 33.

On the other hand, the TG 113, based on the readout start signal outputted once in each period T from the driving signal generation section 34, generates an image pickup control signal for completing exposure of the line L1 in a frame F3 and starting readout of the line L1 in the frame F3 at a time T4 corresponding to a timing substantially immediately after the start of exposure of the line LN in the frame F3, and outputs the generated image pickup control signal to the light-receiving section 111.

The light source control section 21 generates a light emission control signal for starting emission of the B light by the second LED in the special-light LED group 222 at a time T5 corresponding to a timing after a delay period Δt1 has elapsed from the time T4 at which the readout start signal was inputted from the driving signal generation section 34, and for terminating the emission of the B light by the second LED in the special-light LED group 222 at a time T6 corresponding to a timing after a light emission period t1 has elapsed from the time T5, and outputs the generated light emission control signal to the LED unit 22 and the image adding section 32A.

The light source control section 21, when generating the above-described light emission control signal, sets the light emission period t1 so as to include the time T6 in the period after the readout of the line L1 of the light-receiving section 111 has been completed for the frame F3 until before readout of the line L1 is started for a frame F4 (for example, immediately before the readout of the line L1 is started for the frame F4). In addition, when generating the above-described light emission control signal, the light source control section 21 sets the delay period Δt1 such that the relation of Δt1<T−t1 is established, that is, the delay period Δt1 is smaller than the difference between the exposure period T of the line L1 in the frame F3 and the light emission period t1 of the second LED.

In response to the output of the above-described light emission control signal, in the light emission period t1 bridging over two frames, i.e., the frames F3 and F4, the B light emitted from (the second LED in) the special-light LED group 222 is supplied to the light guide 5, and further, the object is illuminated with the B light applied through the light guide 5.

The light-receiving section 111 performs image pickup operation using the rolling-shutter method based on the image pickup control signal outputted from the TG 113, to thereby receive the return light of the B light applied to the object in the light emission period t1, and generates an electric signal corresponding to the received return light, to output the generated electric signal.

The signal processing section 112 performs signal processing such as A/D conversion processing on the electric signal outputted from the light-receiving section 111, to sequentially generate image data for the two frames F3 and F4 and output the generated image data for the two frames to the selector 31.

The selector 31 operates so as to output the image data outputted from the signal processing section 112 to the image adding section 32A, based on the system control signal outputted from the control section 35.

The selector 321, based on the light emission control signal outputted from the light source control section 21 and the readout start signal outputted from the driving signal generation section 34, recognizes the image data inputted first after the start of the emission of the B light by the second LED in the special-light LED group 222, as the image data for the frame F3, and causes the memory 324 to store the image data for the frame F3. In addition, based on the light emission control signal outputted from the light source control section 21 and the readout start signal outputted from the driving signal generation section 34, the selector 321 recognizes the image data inputted secondly after the start of the emission of the B light by the second LED in the special-light LED group 222, as the image data for the frame F4, and causes the memory 325 to store the image data for the frame F4.

Based on the light emission control signal outputted from the light source control section 21 and the readout start signal outputted from the driving signal generation section 34, when the selector 327 detects that the image data for the frame F3 obtained following the emission of the B light is stored in the memory 324 and the image data for the frame F4 obtained following the emission of the B light is stored in the memory 325, the selector 327 simultaneously outputs the image data for the frames F3 and F4 to the adding circuit 329.

The adding circuit 329 performs adding processing on the image data for the frames F3 and F4 which are simultaneously outputted from the selector 327, and outputs the image data subjected to the adding processing to the image processing section 33.

The image processing section 33, based on the system control signal outputted from the control section 35, performs image processing corresponding to the special light observation mode on the two image data outputted from the adding circuits 328 and 329, to thereby generate a video signal and output the generated video signal to the monitor 4. Specifically, the image processing section 33 synthesizes the two image data outputted from the adding circuits 328 and 329, for example, and performs processing such as white balance adjustment and gain adjustment on the synthesized image data, to thereby generate a video signal and output the generated video signal to the monitor 4.

As described above, the image pickup system 101 according to the present embodiment is configured to perform processing for adding and synthesizing the images for the two frames (the frames F1 and F2) obtained following the emission of the A light and processing for adding and synthesizing the images for the two frames (for the frames F3 and F4) obtained following the emission of the B light, while performing the image pickup operation using the rolling-shutter method in the special light observation mode. Therefore, the image pickup system 101 of the present embodiment is capable of suppressing the brightness unevenness of an image caused by the image pickup operation using the rolling-shutter method employed in the (light-receiving section 111 of) the CMOS image sensor 11.

In addition, the image pickup system 101 according to the present embodiment is capable of displaying an observation image having no brightness unevenness on the monitor 4, without a need for performing complicated control of changing the operation method of the CMOS image sensor 11 in accordance with the switching of the observation mode, for example.

In addition, according to the image pickup system 101 of the present embodiment, the above-described control is performed in the light source control section 21, thereby enabling the object to be irradiated with the A light and the B light at the timing at which the number of adding frames, which is required when an observation image having no brightness unevenness (and color mixture) is generated and displayed on the monitor 4, is minimized. That is, according to the image pickup system 101 of the present embodiment, the above-described control is performed in the light source control section 21, thereby capable of minimizing, as much as possible, a decrease in the frame rate when an observation image having no brightness unevenness and color mixture is generated and displayed on the monitor 4.

Figure 4:
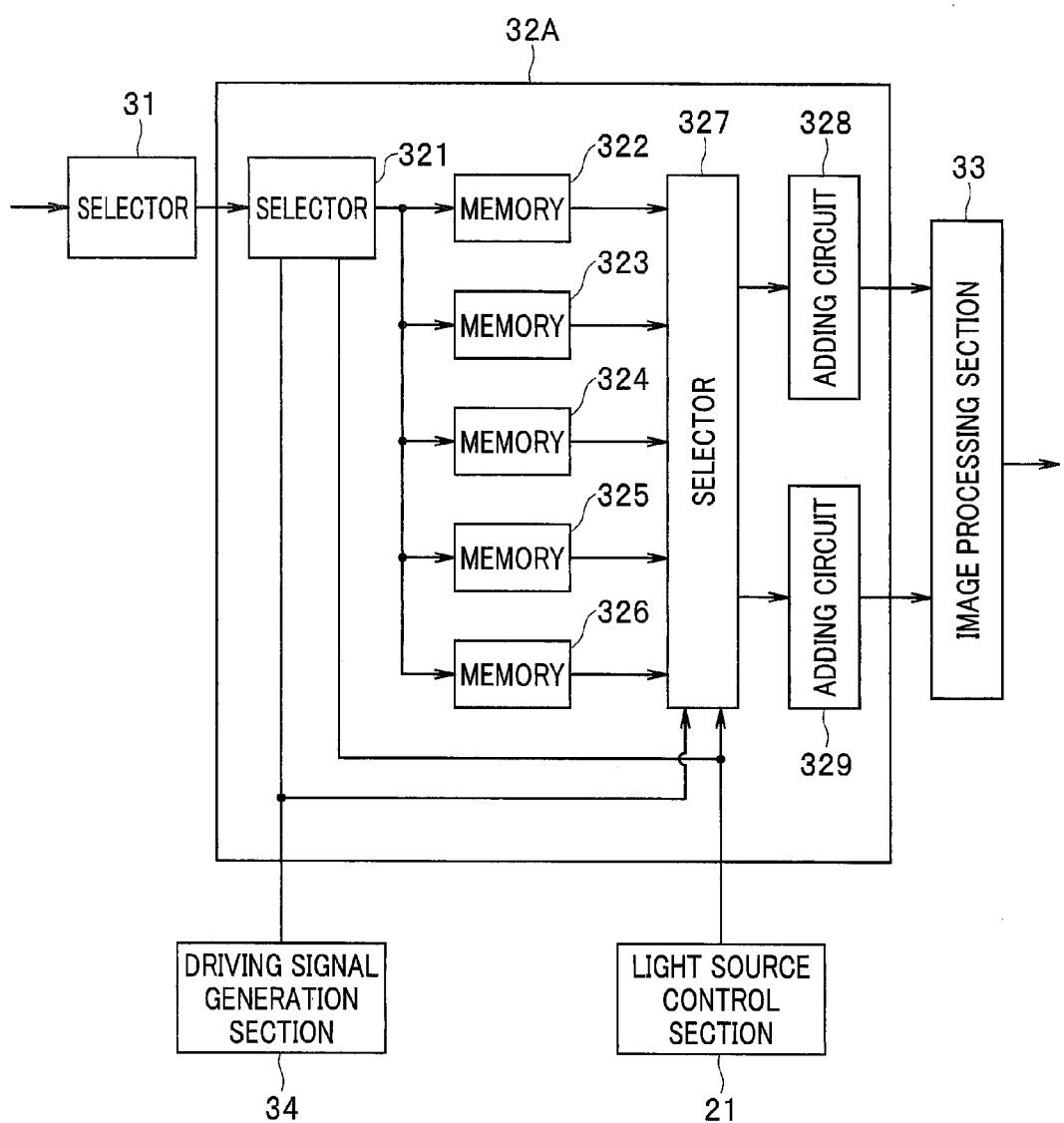
FIG. 4 is a block diagram showing an example of a specific configuration of an image adding section according to a modified example of the first embodiment.

Note that, according to the present embodiment, when the emission period of the A light is required to be sufficiently longer than the emission period of the B light in order to adjust the color balance of the observation image displayed on the monitor 4, for example, the image pickup system 101 may be configured by using an image adding section 32A exemplified in FIG. 4, instead of the image adding section 32 exemplified in FIG. 2. FIG. 4 is a block diagram showing an example of a specific configuration of an image adding section according to a modified example of the first embodiment.

As shown in FIG. 4, the image adding section 32A is configured by including, at the subsequent stage of the selector 321 of the image adding section 32, a memory 326 having the same function as that of the memories 322 to 325.

Figure 5:
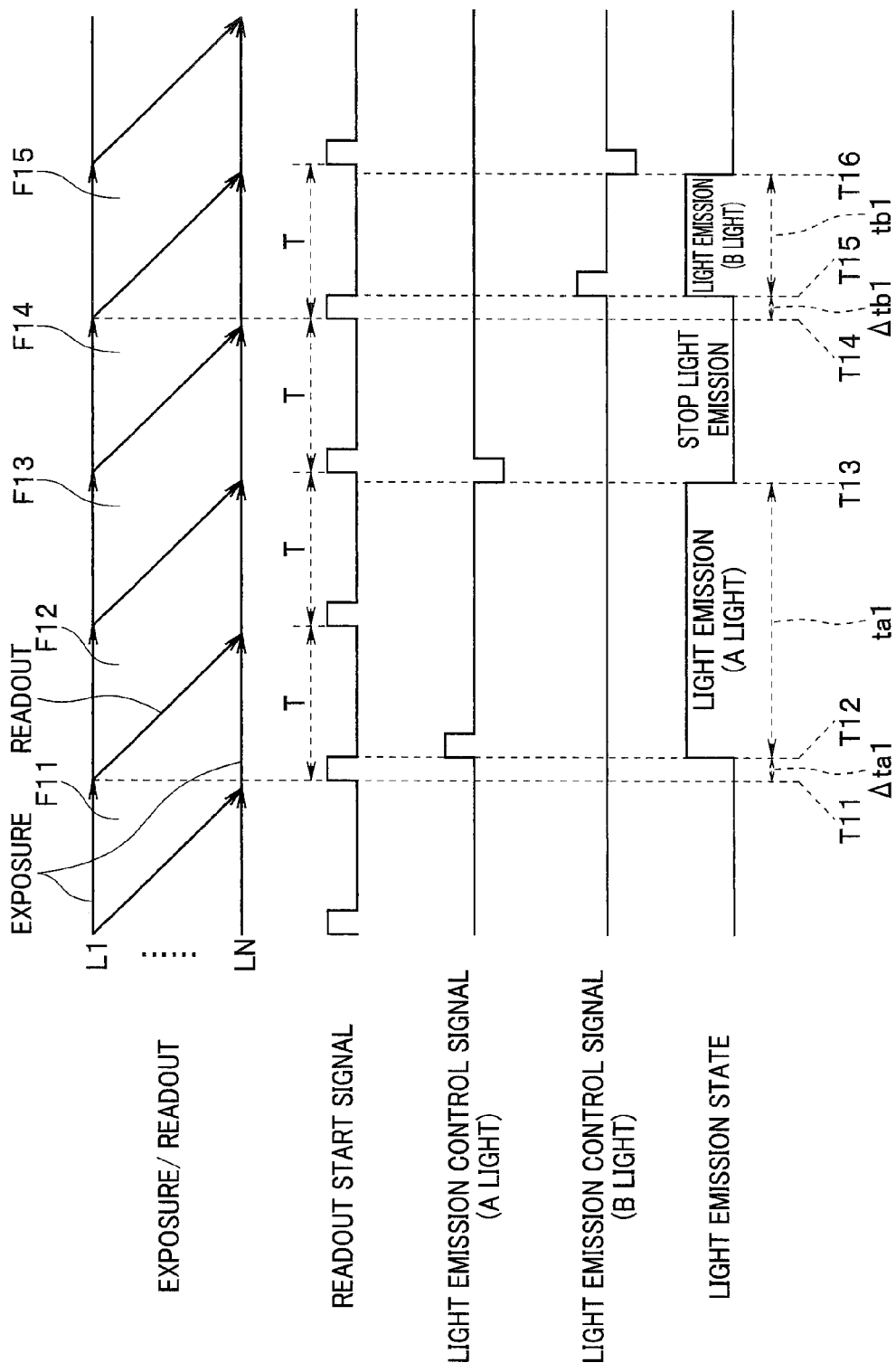
FIG. 5 describes an operation performed in the image pickup system according to the modified example of the first embodiment.

Now, description will be made on the specific operation performed when the image pickup system 101 provided with the image adding section 32A is set to the special light observation mode. FIG. 5 describes an operation performed in the image pickup system according to the modified example of the first embodiment. Note that, hereinafter description will be made by taking a case where the emission period of the A light is longer than the exposure period T for one frame and shorter than the exposure period 2T for two frames, as an example.

The TG 113, based on the readout start signal outputted once in each period T from the driving signal generation section 34, generates an image pickup control signal for completing exposure of the line L1 in a frame F11 and starting readout of the line L1 in the frame F11 at a time T11 corresponding to a timing substantially immediately after the start of exposure of the line LN in the frame F1, and outputs the generated image pickup control signal to the light-receiving section 111. The light source control section 21 generates a light emission control signal for starting the emission of the A light by the first LED in the special-light LED group 222 at a time T12 corresponding to a timing after a delay period Δta1 has elapsed from the time T11 at which the readout start signal was inputted from the driving signal generation section 34, and for terminating the emission of the A light by the first LED in the special-light LED group 222 at a time T13 corresponding to a timing after a light emission period ta1 has elapsed from the time T12, and outputs the generated light emission control signal to the LED unit 22 and the image adding section 32.

The light source control section 21, when generating the above-described light emission control signal, sets the light emission period ta1 so as to include the time T13 in the period after the readout of the line L1 of the light-receiving section 111 has been completed for a frame F12 until before the readout of the line L1 is started for a frame F13 (for example, immediately before the readout of the line L1 is started for the frame F13). In addition, when generating the above-described light emission control signal, the light source control section 21 sets the delay period Δta1 such that the relation of Δta1<2T−ta1 is established, that is, the delay period Δta1 is smaller than the difference between the period obtained by doubling the exposure period T of the line L1 in the frame F11 and the light emission period ta1 of the first LED.

In response to the output of the above-described light emission control signal, in the light emission period ta1 bridging over the three frames, i.e., the frames F11, F12, and F13, the A light emitted from (the first LED in) the special-light LED group 222 is supplied to the light guide 5, and further, the object is illuminated with the A light applied through the light guide 5.

The light-receiving section 111 performs image pickup operation using the rolling-shutter method based on the image pickup control signal outputted from the TG 113, to thereby receive the return light of the A light applied to the object in the light emission period ta1, and generates an electric signal corresponding to the received return light, to output the generated electric signal.

The signal processing section 112 performs signal processing such as A/D conversion processing on the electric signal outputted from the light-receiving section 111, to sequentially generate image data for the three frames F11, F12, and F13, and output the generated image data for the three frames to the selector 31.

The selector 31 operates so as to output the image data outputted from the signal processing section 112 to the image adding section 32, based on the system control signal outputted from the control section 35.

The selector 321, based on the light emission control signal outputted from the light source control section 21 and the readout start signal outputted from the driving signal generation section 34, recognizes the image data inputted first after the start of the emission of the A light by the first LED in the special-light LED group 222, as the image data for the frame F11, and causes the memory 322 to store the image data for the frame F11. In addition, based on the light emission control signal outputted from the light source control section 21 and the readout start signal outputted from the driving signal generation section 34, the selector 321 recognizes the image data inputted secondly after the start of the emission of the A light by the first LED in the special-light LED group 222, as the image data for the frame F12, and causes the memory 323 to store the image data for the frame F12. In addition, based on the light emission control signal outputted from the light source control section 21 and the readout start signal outputted from the driving signal generation section 34, the selector 321 recognizes the image data inputted thirdly after the start of the emission of the A light by the first LED in the special-light LED group 222, as the image data for the frame F13, and causes the memory 324 to store the image data for the frame F13.

Based on the light emission control signal outputted from the light source control section 21 and the readout start signal outputted from the driving signal generation section 34, when the selector 327 detects that the image data for the frame F11 obtained following the emission of the A light is stored in the memory 322, the image data for the frame F12 obtained following the emission of the A light is stored in the memory 323, and the image data for the frame F13 obtained following the emission of the A light is stored in the memory 324, the selector 327 simultaneously outputs the image data for the frames F11, F12, and F13 to the adding circuit 328.

The adding circuit 328 performs adding processing on the image data for the frames F11, F12, and F13 which are simultaneously outputted from the selector 327, and outputs the image data subjected to the adding processing to the image processing section 33.

On the other hand, the TG 113, based on the readout start signal outputted once in each period T from the driving signal generation section 34, generates an image pickup control signal for completing exposure of the line L1 in a frame F14 and starting readout of the line L1 in the frame F14 at a time T14 corresponding to a timing substantially immediately after the start of exposure of the line LN in the frame F14, and outputs the generated image pickup control signal to the light-receiving section 111.

The light source control section 21 generates a light emission control signal for starting the emission of the B light by the second LED in the special-light LED group 222 at a time T15 corresponding to a timing after a delay period Δtb1 has elapsed from the time T14 at which the readout start signal was inputted from the driving signal generation section 34, and for terminating the emission of the B light by the second LED in the special-light LED group 222 at a time T16 corresponding to a timing after a light emission period tb1 has elapsed from the time T15, and outputs the generated light emission control signal to the LED unit 22 and the image adding section 32.

The light source control section 21, when generating the above-described light emission control signal, sets the light emission period tb1 so as to include the time T16 in the period after the readout of the line L1 of the light-receiving section 111 has been completed for the frame F14 until before the readout of the line L1 is started for a frame F15 (for example, immediately before the readout of the line L1 is started for the frame F15). In addition, when generating the above-described light emission control signal, the light source control section 21 sets the delay period Δtb1 such that the relation of Δtb1<T−tb1 is established, that is, the delay period Δtb1 is smaller than the difference between the exposure period T of the line L1 in the frame F14 and the light emission period tb1 of the second LED.

In response to the output of the above-described light emission control signal, in the light emission period tb1 bridging over the two frames, i.e., the frames F14 and F15, the B light emitted from (the second LED in) the special-light LED group 222 is supplied to the light guide 5, and further, the object is illuminated with the B light applied through the light guide 5.

The light-receiving section 111 performs image pickup operation using the rolling-shutter method based on the image pickup control signal outputted from the TG 113, to thereby receive the return light of the B light applied to the object in the light emission period tb1, and generates an electric signal corresponding to the received return light, to output the generated electric signal.

The signal processing section 112 performs signal processing such as A/D conversion processing on the electric signal outputted from the light-receiving section 111, to sequentially generate image data for the two frames F14 and F15 and output the generated image data for the two frames to the selector 31.

The selector 31 operates so as to output the image data outputted from the signal processing section 112 to the image adding section 32, based on the system control signal outputted from the control section 35.

The selector 321, based on the light emission control signal outputted from the light source control section 21 and the readout start signal outputted from the driving signal generation section 34, recognizes the image data inputted first after the start of the emission of the B light by the second LED in the special-light LED group 222, as the image data for the frame F14, and causes the memory 325 to store the image data for the frame F14. In addition, based on the light emission control signal outputted from the light source control section 21 and the readout start signal outputted from the driving signal generation section 34, the selector 321 recognizes the image data inputted secondly after the start of the emission of the B light by the second LED in the special-light LED group 222, as the image data for the frame F15, and causes the memory 326 to store the image data for the frame F15.

Based on the light emission control signal outputted from the light source control section 21 and the readout start signal outputted from the driving signal generation section 34, when the selector 327 detects that the image data for the frame F14 obtained following the emission of the B light is stored in the memory 325 and the image data for the frame F15 obtained following the emission of the B light is stored in the memory 326, the selector 327 simultaneously outputs the image data for the frames F14 and F15 to an adding circuit 329.

The adding circuit 329 performs adding processing on the image data for the frames F14 and F15 which are simultaneously outputted from the selector 327, and outputs the image data subjected to the adding processing to the image processing section 33.

The image processing section 33, based on the system control signal outputted from the control section 35, performs image processing corresponding to the special light observation mode on the two image data outputted from the adding circuits 328 and 329, to thereby generate a video signal and output the generated video signal to the monitor 4. Specifically, the image processing section 33 synthesizes the two image data outputted from the adding circuits 328 and 329, for example, and performs processing such as white balance adjustment and gain adjustment on the synthesized image data, to thereby generate a video signal and output the generated video signal to the monitor 4.

As described above, the image pickup system 101 according to the present modified example is configured to perform processing for adding and synthesizing the images for the three frames (the frames F11, F12, and F13) obtained following the emission of the A light and processing for adding and synthesizing the images for the two frames (F14 and F15) obtained following the emission of the B light, while performing image pickup operation using the rolling-shutter method in the special light observation mode. Therefore, the image pickup system 101 of the present modified example is capable of suppressing the brightness unevenness of an image caused by the image pickup operation using the rolling-shutter method employed in the (light-receiving section 111 of) the CMOS image sensor 11.

Second Embodiment

Figure 6:
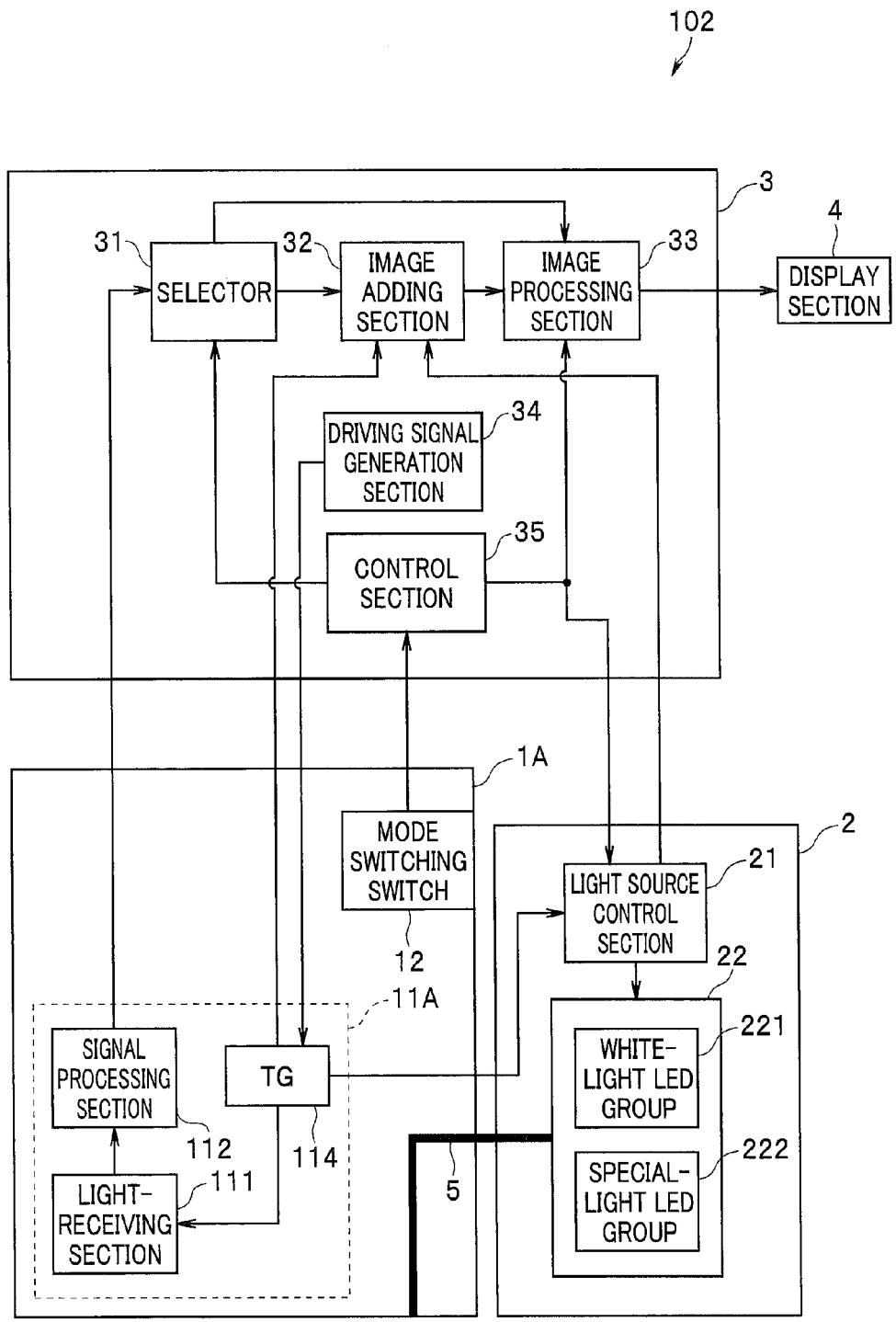
FIG. 6 illustrates a configuration of a main part of an image pickup system according to a second embodiment.
Figure 7:
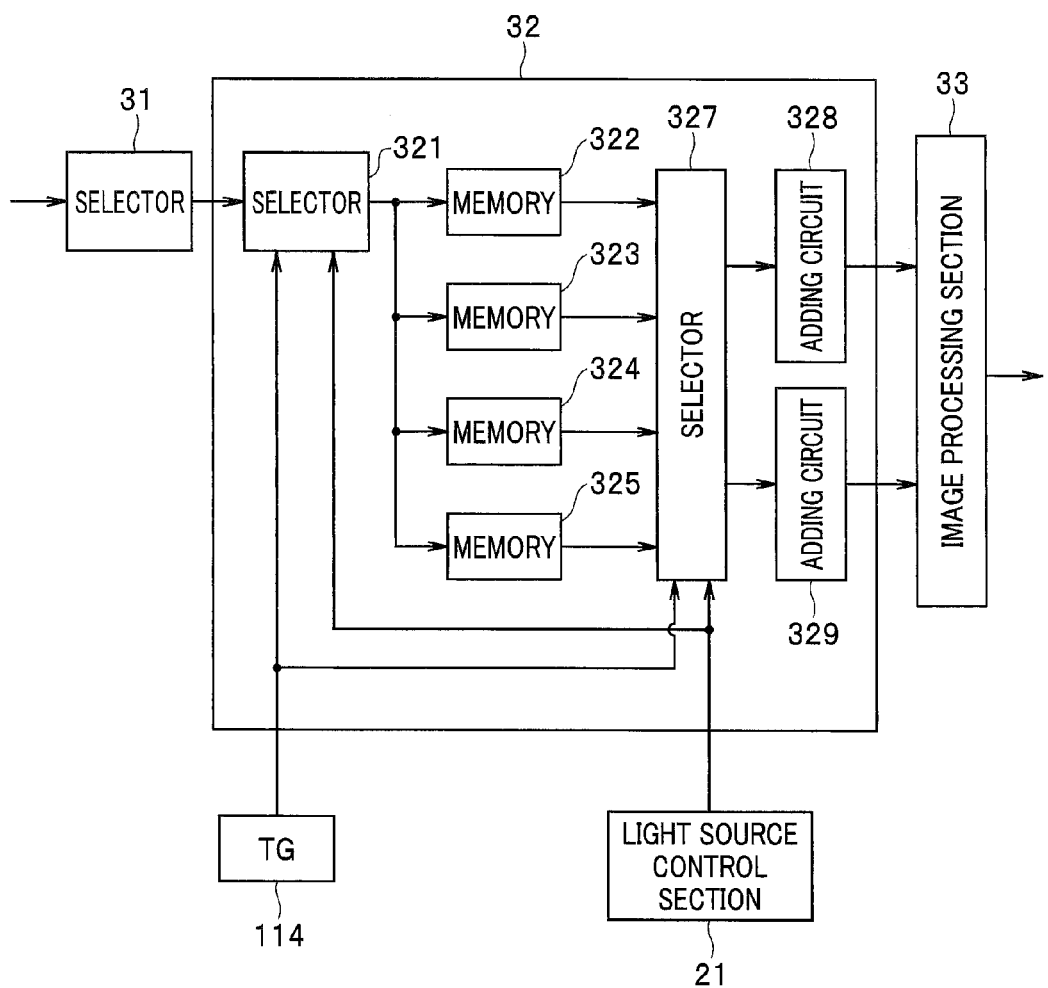
FIG. 7 is a block diagram showing an example of a specific configuration of an image adding section according to the second embodiment.

FIGS. 6 to 10 relate to the second embodiment of the present invention. FIG. 6 illustrates a configuration of a main part of an image pickup system according to the second embodiment. FIG. 7 is a block diagram showing an example of a specific configuration of an image adding section according to the second embodiment.

Note that, in the present embodiment, detailed description related to the parts having the same configurations as those in the first embodiment will be omitted, and description will be mainly made on parts having configurations different from those in the first embodiment.

As shown in FIG. 6, an image pickup system 102 includes an endoscope 1A including a CMOS image sensor 11A and the mode switching switch 12, instead of the endoscope 1 in the image pickup system 101 in the first embodiment.

The CMOS image sensor 11A includes a light-receiving section 111, a signal processing section 112, and a TG 114.

The TG 114 is configured to be able to generate an image pickup control signal similar to the one generated by the TG 113 according to the first embodiment and output the generated image pickup control signal. In addition, as shown in FIGS. 6 and 7, the TG 114 is configured to, at the timing at which readout of the line LN of the light-receiving section 111 has been completed, generate a readout completion signal representing completion of readout for one frame and output the generated readout completion signal to a light source control section 21, a selector 321, and a selector 327.

That is, with the image pickup system 102 according to the present embodiment, the TG 114 includes a function as a trigger signal output section, and the readout completion signal outputted from the TG 114 has a function as a trigger signal.

The driving signal generation section 34 according to the present embodiment generates a readout start signal representing a timing for starting the readout of the line L1 of the light-receiving section 111, once in each period (T+τ) obtained by adding a blank period τ to the period T corresponding to the frame rate related to image obtainment, and outputs the generated readout start signal to the TG 114. Note that the above-described blank period τ is a period generated depending on the performances of the light-receiving section 111 and the TG 114 in the CMOS image sensor 11A, for example, and represents a period from the timing at which exposure of the line LN in one frame has been started until readout of the line L1 in the one frame is started.

Figure 8:
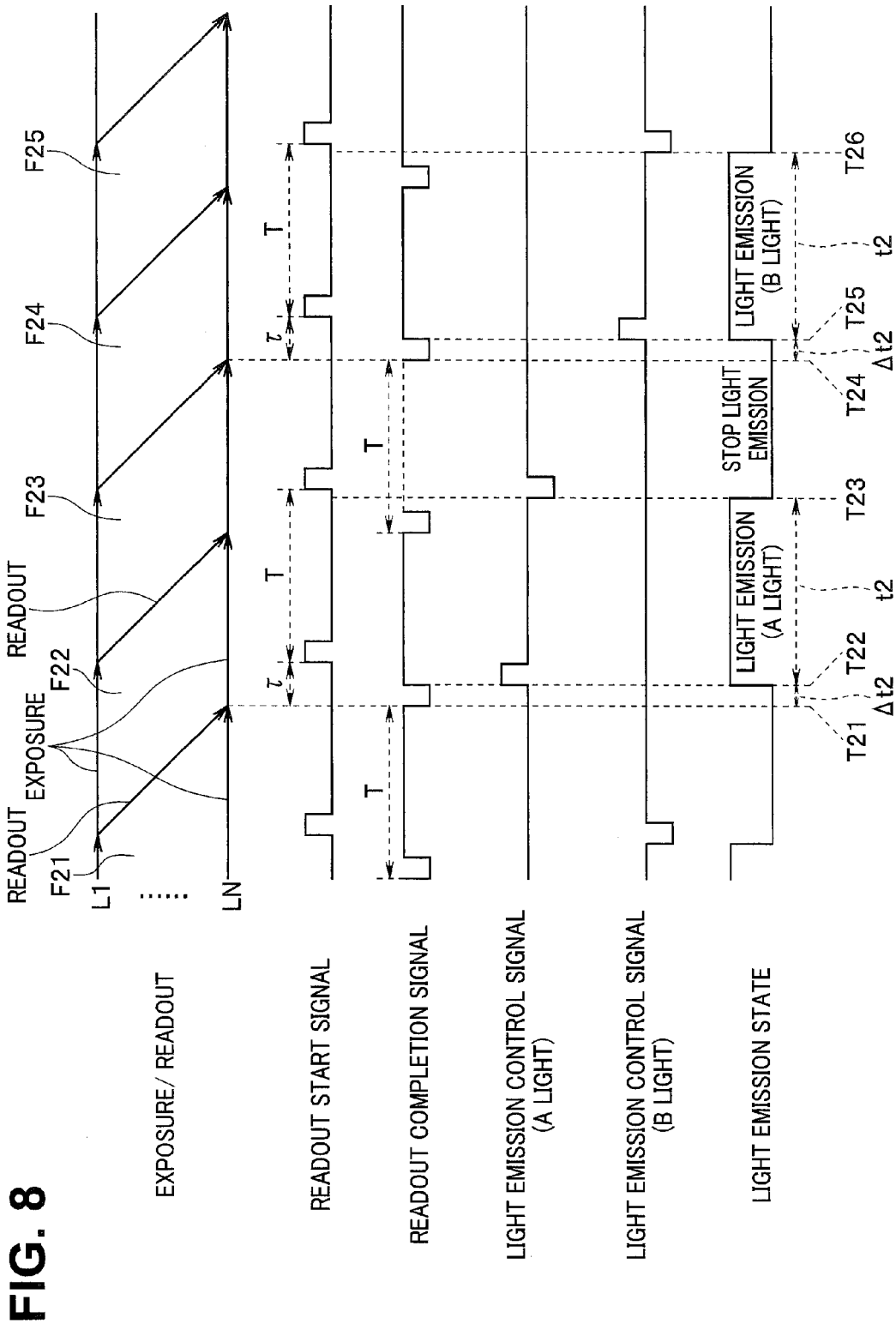
FIG. 8 describes an operation performed in the image pickup system according to the second embodiment.

Next, working of the image pickup system 102 including the configuration as described above will be described. Note that the image pickup system 102 according to the present embodiment is configured to perform, when being set to the white light observation mode, substantially the same operation as the operation performed by the image pickup system 101 according to the first embodiment. Therefore, hereinafter, description on the specific operation performed when the image pickup system 102 is set to the white light observation mode will be omitted and description will be made on the specific operation performed when the image pickup system 102 is set to the special light observation mode. FIG. 8 describes an operation performed in the image pickup system according to the second embodiment.

The TG 114, at a time T21 corresponding to the timing at which the readout of the line LN in a frame F21 has been completed, generates a readout completion signal representing the timing and outputs the generated readout completion signal to the light source control section 21, the selector 321, and the selector 327.

The light source control section 21 generates a light emission control signal for starting the emission of the A light by the first LED in the special-light LED group 222 at a time T22 corresponding to a timing after a delay period Δt2 has elapsed from the time T21 at which the readout completion signal was inputted from the TG 114, and for terminating the emission of the A light by the first LED in the special-light LED group 222 at a time T23 corresponding to a timing after a light emission period t2 has elapsed from the time T22, and outputs the generated light emission control signal to the LED unit 22 and the image adding section 32.

The light source control section 21, when generating the above-described light emission control signal, sets the light emission period t2 so as to include the time T23 in the period after the readout of the line L1 of the light-receiving section 111 has been completed for a frame F22 until before the readout of the line L1 is started for a frame F23 (for example, immediately before the readout of the line L1 is started for the frame F23). In addition, when generating the above-described light emission control signal, the light source control section 21 sets the delay period Δt2 such that the relation of Δt2<(T+τ)−t2 is established, that is, the delay period Δt2 is smaller than the difference between the period (T+τ), which is obtained by adding the blank period τ to the exposure period T of the line LN in the frame F21, and the light emission period t2 of the first LED.

In response to the output of the above-described light emission control signal, in the light emission period t2 bridging over the two frames, i.e., the frames F22 and F23, the A light emitted from (the first LED in) the special-light LED group 222 is supplied to the light guide 5, and further, the object is illuminated with the A light applied through the light guide 5.

The light-receiving section 111 performs image pickup operation using the rolling-shutter method based on the image pickup control signal outputted from the TG 114, to thereby receive the return light of the A light applied to the object in the light emission period t2, and generates an electric signal corresponding to the received return light, to output the generated electric signal.

The signal processing section 112 performs signal processing such as A/D conversion processing on the electric signal outputted from the light-receiving section 111, to sequentially generate image data for the two frames F22 and F23 and output the generated image data for the two frames to the selector 31.

The selector 31 operates so as to output the image data outputted from the signal processing section 112 to the image adding section 32, based on the system control signal outputted from the control section 35.

The selector 321, based on the light emission control signal outputted from the light source control section 21 and the readout completion signal outputted from the TG 114, recognizes the image data inputted first after the start of the emission of the A light by the first LED in the special-light LED group 222, as the image data for the frame F22, and causes the memory 322 to store the image data for the frame F22. In addition, based on the light emission control signal outputted from the light source control section 21 and the readout completion signal outputted from the TG 114, the selector 321 recognizes the image data inputted secondly after the start of the emission of the A light by the first LED in the special-light LED group 222, as the image data for the frame F23, and causes the memory 323 to store the image data for the frame F23.

Based on the light emission control signal outputted from the light source control section 21 and the readout completion signal outputted from the TG 114, when the selector 327 detects that the image data for the frame F22 obtained following the emission of the A light is stored in the memory 322 and the image data for the frame F23 obtained following the emission of the A light is stored in the memory 323, the selector 327 simultaneously outputs the image data for the frames F23 and F22 to the adding circuit 328.

The adding circuit 328 performs adding processing on the image data for the frames F22 and F23 which are simultaneously outputted from the selector 327, and outputs the image data subjected to the adding processing to the image processing section 33.

On the other hand, the TG 114, at a time T24 corresponding to the timing at which the readout of the line LN in the frame F23 has been completed, generates a readout completion signal representing the timing and outputs the generated readout completion signal to the light source control section 21, the selector 321, and the selector 327.

The light source control section 21 generates a light emission control signal for starting the emission of the B light by the second LED in the special-light LED group 222 at a time T25 corresponding to a timing after a delay period Δt2 has elapsed from the time T24 at which the readout completion signal was inputted from the TG 114, and for terminating the emission of the B light by the second LED in the special-light LED group 222 at a time T26 corresponding to a timing after a light emission period t2 has elapsed from the time T25, and outputs the generated light emission control signal to the LED unit 22 and the image adding section 32.

The light source control section 21, when generating the above-described light emission control signal, sets the light emission period t2 so as to include the time T26 in the period after the readout of the line L1 of the light-receiving section 111 has been completed for a frame F24 until before the readout of the line L1 is started for a frame F25 (for example, immediately before the readout of the line L1 is started for the frame F25). In addition, when generating the above-described light emission control signal, the light source control section 21 sets the delay period Δt2 such that the relation of Δt2<(T+τ)−t2 is established, that is, the delay period Δt2 is smaller than the difference between the period (T+τ), which is obtained by adding the blank period τ to the exposure period T of the line LN in the frame F23, and the light emission period t2 of the second LED.

In response to the output of the above-described light emission control signal, in the light emission period t2 bridging over the two frames, i.e., the frames F24 and F25, the B light emitted from (the second LED in) the special-light LED group 222 is supplied to the light guide 5, and further, the object is illuminated with the B light applied through the light guide 5.

The light-receiving section 111 performs image pickup operation using the rolling-shutter method based on the image pickup control signal outputted from the TG 114, to thereby receive the return light of the B light applied to the object in the light emission period t2, and generates an electric signal corresponding to the received return light, to output the generated electric signal.

The signal processing section 112 performs signal processing such as A/D conversion processing on the electric signal outputted from the light-receiving section 111, to sequentially generate image data for the two frames F24 and F25 and output the generated image data for the two frames to the selector 31.

The selector 31 operates so as to output the image data outputted from the signal processing section 112 to the image adding section 32, based on the system control signal outputted from the control section 35.

The selector 321, based on the light emission control signal outputted from the light source control section 21 and the readout completion signal outputted from the TG 114, recognizes the image data inputted first after the start of the emission of the B light by the second LED in the special-light LED group 222, as the image data for the frame F24, and causes the memory 324 to store the image data for the frame F24. In addition, based on the light emission control signal outputted from the light source control section 21 and the readout completion signal outputted from the TG 114, the selector 321 recognizes the image data inputted secondly after the start of the emission of the B light by the second LED in the special-light LED group 222, as the image data for the frame F25, and causes the memory 325 to store the image data for the frame F25.

Based on the light emission control signal outputted from the light source control section 21 and the readout completion signal outputted from the TG 114, when the selector 327 detects that the image data for the frame F24 obtained following the emission of the B light is stored in the memory 324 and the image data for the frame F25 obtained following the emission of the B light is stored in the memory 325, the selector 327 simultaneously outputs the image data for the frames F24 and F25 to the adding circuit 329.

The adding circuit 329 performs adding processing on the image data for the frames F24 and F25 which are simultaneously outputted from the selector 327, and outputs the image data subjected to the adding processing to the image processing section 33.

The image processing section 33, based on the system control signal outputted from the control section 35, performs image processing corresponding to the special light observation mode on the two image data outputted from the adding circuits 328 and 329, to thereby generate a video signal and output the generated video signal to the monitor 4. Specifically, the image processing section 33 synthesizes the two image data outputted from the adding circuits 328 and 329, for example, and performs processing such as white balance adjustment and gain adjustment on the synthesized image data, to thereby generate a video signal and output the generated video signal to the monitor 4.

As described above, the image pickup system 102 according to the present embodiment is configured to perform processing for adding and synthesizing the images for the two frames (the frames F22 and F23) obtained following the emission of the A light and processing for adding and synthesizing the images for the two frames (for the frames F24 and F25) obtained following the emission of the B light, while performing the image pickup operation using the rolling-shutter method in the special light observation mode. Therefore, the image pickup system 102 of the present embodiment is capable of suppressing the brightness unevenness of an image caused by the image pickup operation using the rolling-shutter method employed in the (light-receiving section 111 of) the CMOS image sensor 11A.

In addition, the image pickup system 102 according to the present embodiment is capable of displaying an observation image having no brightness unevenness on the monitor 4, without a need for performing complicated control of changing the operation method of the CMOS image sensor 11A in accordance with the switching of the observation mode, for example.

In addition, according to the image pickup system 102 of the present embodiment, the above-described control is performed in the light source control section 21, thereby enabling the object to be irradiated with the A light and the B light at the timing at which the number of adding frames, which is required when an observation image having no brightness unevenness (and color mixture) is generated and displayed on the monitor 4, is minimized, while taking a presence of the blank period $\tau$ into consideration. That is, according to the image pickup system 102 of the present embodiment, the above-described control is performed in the light source control section 21, thereby capable of minimizing, as much as possible, a decrease in the frame rate when an observation image having no brightness unevenness and color mixture is generated and displayed on the monitor 4.

Figure 9:
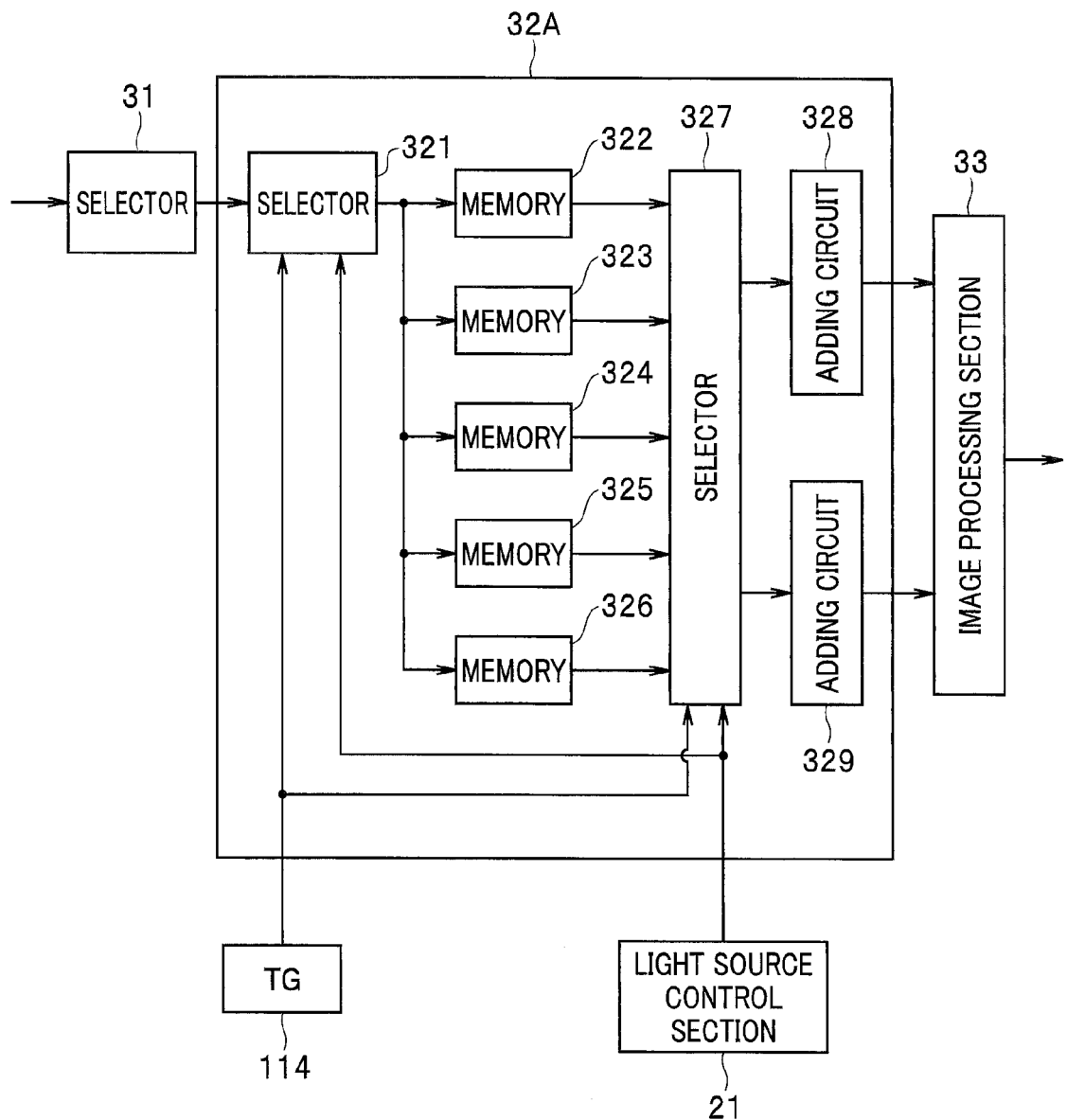
FIG. 9 is a block diagram showing an example of a specific configuration of an image adding section according to a modified example of the second embodiment.

Note that, according to the present embodiment, when the emission period of the A light is required to be sufficiently longer than the emission period of the B light in order to adjust the color balance of the observation image displayed on the monitor 4, for example, the image pickup system 102 may be configured by using an image adding section 32A (having substantially the same configuration as that described in the first embodiment) exemplified in FIG. 9, instead of the image adding section 32 exemplified in FIG. 7. FIG. 9 is a block diagram showing an example of a specific configuration of an image adding section according to a modified example of the second embodiment.

Figure 10:
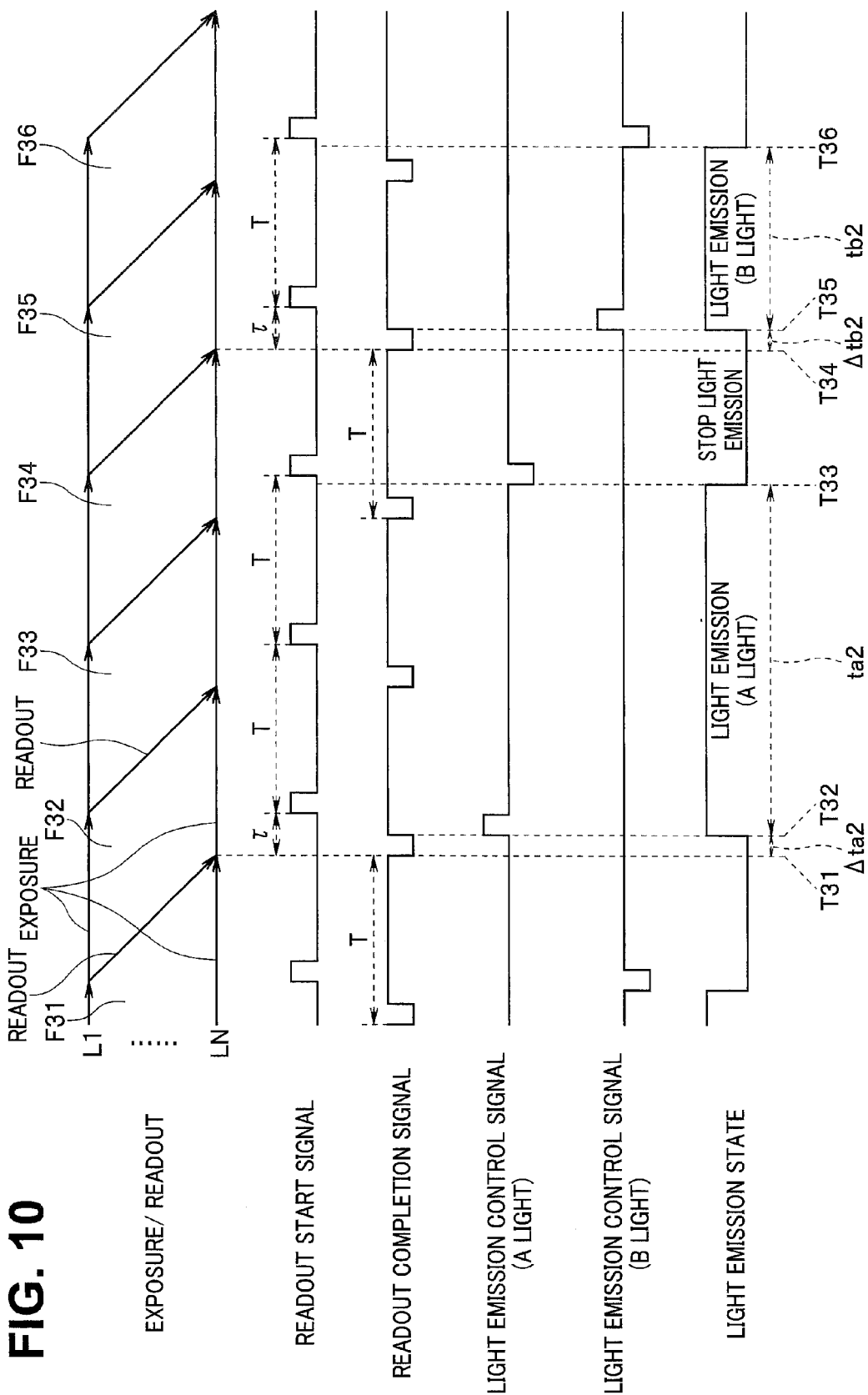
FIG. 10 describes an operation performed in the image pickup system according to the modified example of the second embodiment.

Now, description will be made on the specific operation performed when the image pickup system 102 provided with the image adding section 32A is set to the special light observation mode. FIG. 10 describes an operation performed in the image pickup system according to the modified example of the second embodiment. Note that, hereinafter description will be made by taking a case where the emission period of the A light is longer than the period (T+$\tau$) obtained by adding the blank period $\tau$ to the exposure period T for one frame and shorter than a period (2T+$\tau$) obtained by adding the blank period $\tau$ to the exposure period 2T for two frames, as an example.

The TG 114, at a time T31 corresponding to the timing at which the readout of the line LN in a frame F31 has been completed, generates a readout completion signal representing the timing and outputs the generated readout completion signal to the light source control section 21, the selector 321, and the selector 327.

The light source control section 21 generates a light emission control signal for starting the emission of the A light by the first LED in the special-light LED group 222 at a time T32 corresponding to a timing after a delay period $\Delta$ta2 has elapsed from the time T31 at which the readout completion signal was inputted from the TG 114, and for terminating the emission of the A light by the first LED in the special-light LED group 222 at a time T33 corresponding to a timing after a light emission period ta2 has elapsed from the time T32, and outputs the generated light emission control signal to the LED unit 22 and the image adding section 32.

The light source control section 21, when generating the above-described light emission control signal, sets the light emission period ta2 so as to include the time T33 in the period after the readout of the line L1 of the light-receiving section 111 has been completed for a frame F33 until before the readout of the line L1 is started for a frame F34 (for example, immediately before the readout of the line L1 is started for the frame F34). In addition, when generating the above-described light emission control signal, the light source control section 21 sets the delay period $\Delta$ta2 such that the relation of $\Delta$ta2<(2T+$\tau$)−ta2 is established, that is, the delay period $\Delta$ta2 is smaller than the difference between the period (2T+$\tau$), which is obtained by adding the blank period T to the period obtained by doubling the exposure period T of the line L1 in the frame F11, and the light emission period ta2 of the first LED.

In response to the output of the above-described light emission control signal, in the light emission period ta2 bridging over the three frames, i.e., the frames F32, F33 and F34, the A light emitted from (the first LED in) the special-light LED group 222 is supplied to the light guide 5, and further, the object is illuminated with the A light applied through the light guide 5.

The light-receiving section 111 performs image pickup operation using the rolling-shutter method based on the image pickup control signal outputted from the TG 114, to thereby receive the return light of the A light applied to the object in the light emission period ta2, and generates an electric signal corresponding to the received return light, to output the generated electric signal.

The signal processing section 112 performs signal processing such as A/D conversion processing on the electric signal outputted from the light-receiving section 111, to sequentially generate image data for the three frames F32, F33, and F34, and output the generated image data for the three frames to the selector 31.

The selector 31 operates so as to output the image data outputted from the signal processing section 112 to the image adding section 32, based on the system control signal outputted from the control section 35.

The selector 321, based on the light emission control signal outputted from the light source control section 21 and the readout completion signal outputted from the TG 114, recognizes the image data inputted first after the start of the emission of the A light by the first LED in the special-light LED group 222, as the image data for a frame F32, and causes the memory 322 to store the image data for the frame F32. Further, based on the light emission control signal outputted from the light source control section 21 and the readout completion signal outputted from the TG 114, the selector 321 recognizes the image data inputted secondly after the start of the emission of the A light by the first LED in the special-light LED group 222, as the image data for the frame F33, and causes the memory 323 to store the image data for the frame F33. Furthermore, based on the light emission control signal outputted from the light source control section 21 and the readout completion signal outputted from the TG 114, the selector 321 recognizes the image data inputted thirdly after the start of the emission of the A light by the first LED in the special-light LED group 222, as the image data for the frame F34, and causes the memory 324 to store the image data for the frame F34.

Based on the light emission control signal outputted from the light source control section 21 and the readout completion signal outputted from the TG 114, when the selector 327 detects that the image data for the frame F32 obtained following the emission of the A light is stored in the memory 322, the image data for the frame F33 obtained following the emission of the A light is stored in the memory 323, and the image data for the frame F34 obtained following the emission of the A light is stored in the memory 324, the selector 327 simultaneously outputs the image data for the frames F32, F33 and F34 to the adding circuit 328.

The adding circuit 328 performs adding processing on the image data for the frames F32, F33 and F34 which are simultaneously outputted from the selector 327, and outputs the image data subjected to the adding processing to the image processing section 33.

On the other hand, the TG 114, at a time T34 corresponding to the timing at which the readout of the line LN in the frame F34 has been completed, generates a readout completion signal representing the timing and outputs the generated readout completion signal to the light source control section 21, the selector 321, and the selector 327.

The light source control section 21 generates a light emission control signal for starting the emission of the B light by the second LED in the special-light LED group 222 at a time T35 corresponding to a timing after a delay period Δtb2 has elapsed from the time T34 at which the readout completion signal was inputted from the TG 114, and for terminating the emission of the B light by the second LED in the special-light LED group 222 at a time T36 corresponding to a timing after a light emission period tb2 has elapsed from the time T35, and outputs the generated light emission control signal to the LED unit 22 and the image adding section 32. The light source control section 21, when generating the above-described light emission control signal, sets the light emission period tb2 so as to include the time T36 in the period after the readout of the line L1 of the light-receiving section 111 has been completed for a frame F35 until before the readout of the line L1 is started for the frame F36 (for example, immediately before the readout of the line L1 is started for the frame F36). In addition, when generating the above-described light emission control signal, the light source control section 21 sets the delay period Δtb2 such that the relation of Δtb2<(T+τ)−tb2 is established, that is, the delay period Δtb2 is smaller than the difference between the period (T+τ), which is obtained by adding the blank period τ to the exposure period T of the line LN in the frame F34, and the light emission period tb2 of the second LED.

In response to the output of the above-described light emission control signal, in the light emission period tb2 bridging over the two frames, i.e., the frames F35 and F36, the B light emitted from (the second LED in) the special-light LED group 222 is supplied to the light guide 5, and further, the object is illuminated with the B light applied through the light guide 5.

The light-receiving section 111 performs image pickup operation using the rolling-shutter method based on the image pickup control signal outputted from the TG 114, to thereby receive the return light of the B light applied to the object in the light emission period tb2, and generates an electric signal corresponding to the received return light, to output the generated electric signal.

The signal processing section 112 performs signal processing such as A/D conversion processing on the electric signal outputted from the light-receiving section 111, to sequentially generate image data for the two frames F35 and F36 and output the generated image data for the two frames to the selector 31.

The selector 31 operates so as to output the image data outputted from the signal processing section 112 to the image adding section 32, based on the system control signal outputted from the control section 35.

The selector 321, based on the light emission control signal outputted from the light source control section 21 and the readout completion signal outputted from the TG 114, recognizes the image data inputted first after the start of the emission of the B light by the second LED in the special-light LED group 222, as the image data for the frame F35, and causes the memory 325 to store the image data for the frame F35. In addition, based on the light emission control signal outputted from the light source control section 21 and the readout completion signal outputted from the TG 114, the selector 321 recognizes the image data inputted secondly after the start of the emission of the B light by the second LED in the special-light LED group 222, as the image data for the frame F36, and causes the memory 326 to store the image data for the frame F36.

Based on the light emission control signal outputted from the light source control section 21 and the readout completion signal outputted from the TG 114, when the selector 327 detects that the image data for the frame F35 obtained following the emission of the B light is stored in the memory 325 and the image data for the frame F36 obtained following the emission of the B light is stored in the memory 326, the selector 327 simultaneously outputs the image data for the frames F35 and F36 to the adding circuit 329.

The adding circuit 329 performs adding processing on the image data for the frames F35 and F36 which are simultaneously outputted from the selector 327, and outputs the image data subjected to the adding processing to the image processing section 33.

The image processing section 33, based on the system control signal outputted from the control section 35, performs image processing corresponding to the special light observation mode on the two image data outputted from the adding circuits 328 and 329, to thereby generate a video signal and output the generated video signal to the monitor 4. Specifically, the image processing section 33 synthesizes the two image data outputted from the adding circuits 328 and 329, for example, and performs processing such as white balance adjustment and gain adjustment on the synthesized image data, to thereby generate a video signal and output the generated video signal to the monitor 4.

As described above, the image pickup system 102 according to the present modified example is configured to perform processing for adding and synthesizing the images for the three frames (the frames F32, F33, and F34) obtained following the emission of the A light and processing for adding and synthesizing the images for the two frames (the frames F35 and F36) obtained following the emission of the B light, while performing image pickup operation using the rolling-shutter method in the special light observation mode. Therefore, the image pickup system 102 of the present modified example is capable of suppressing the brightness unevenness of an image caused by the image pickup operation using the rolling-shutter method employed in the (light-receiving section 111 of) the CMOS image sensor 11.

Third Embodiment

Figure 11:
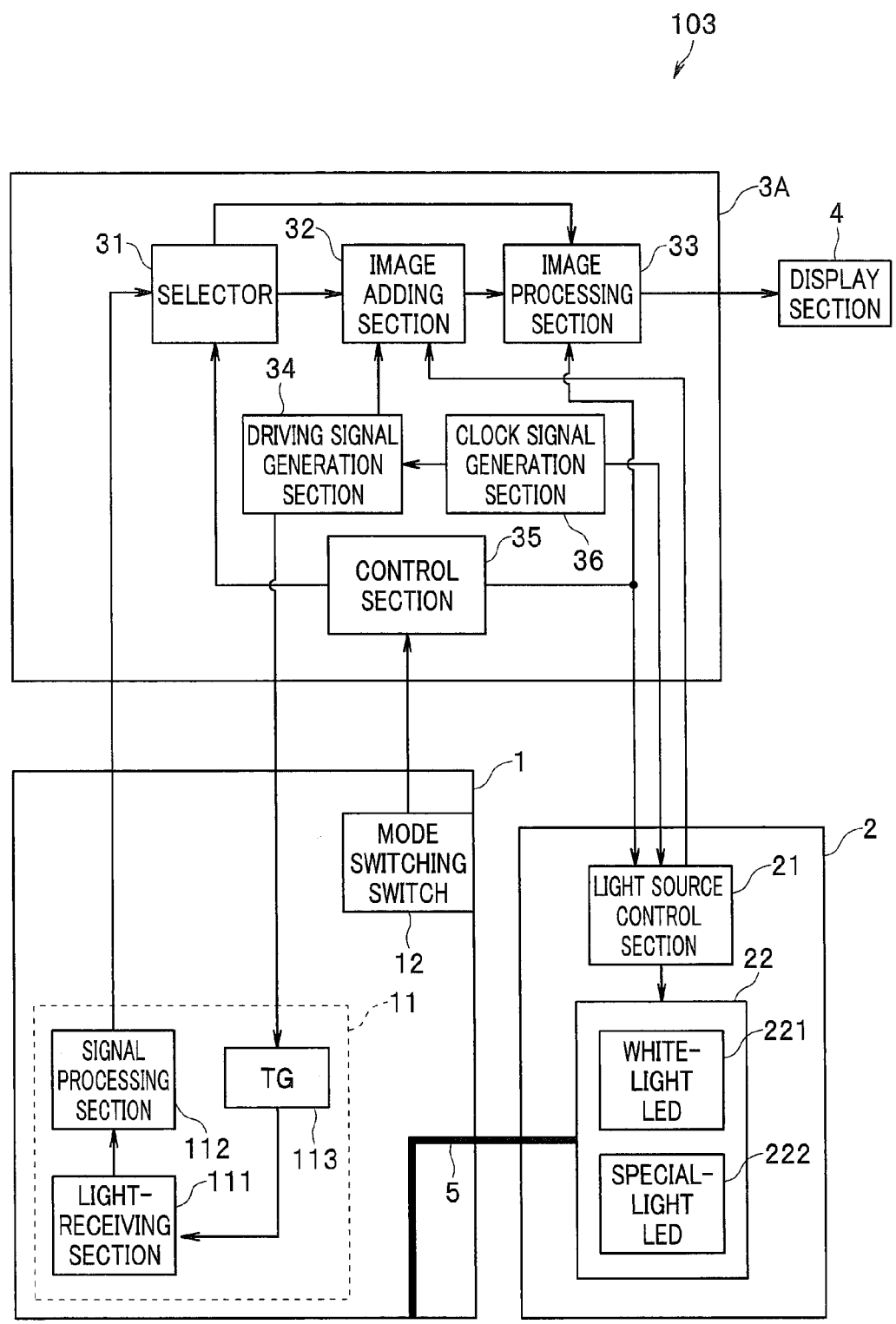
FIG. 11 illustrates a configuration of a main part of an image pickup system according to a third embodiment.
Figure 12:
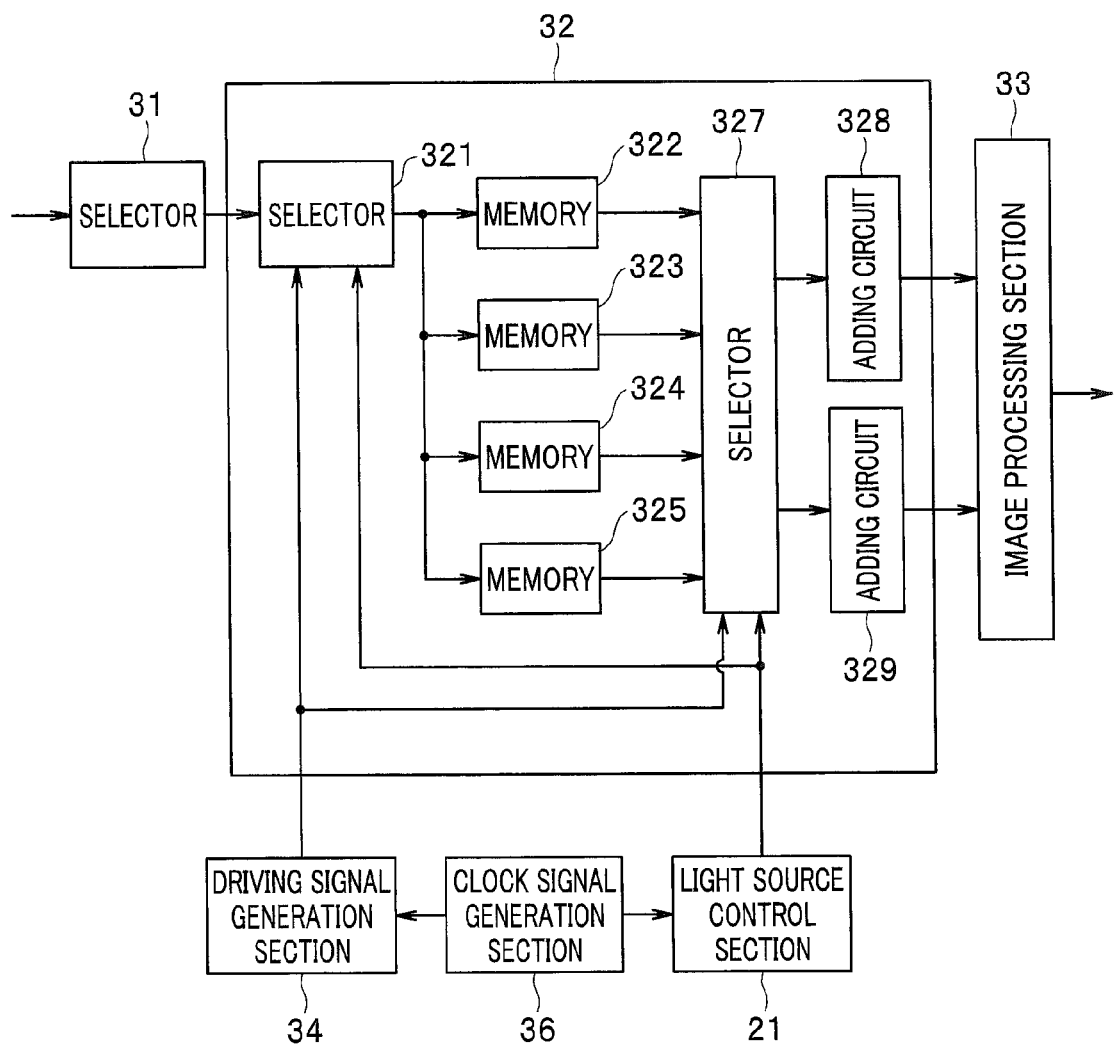
FIG. 12 is a block diagram showing an example of a specific configuration of an image adding section according to the third embodiment.

FIGS. 11 to 15 relate to the third embodiment of the present invention. FIG. 11 illustrates a configuration of a main part of an image pickup system according to the third embodiment. FIG. 12 is a block diagram showing an example of a specific configuration of an image adding section according to the third embodiment.

Note that, in the present embodiment, detailed description related to the parts having the same configurations as those in at least either the first embodiment or the second embodiment will be omitted, and description will be mainly made on parts having configurations different from those in both of the first embodiment and the second embodiment.

As shown in FIG. 11, an image pickup system 103 includes a processor 3A instead of the processor 3 provided in the image pickup system 101 according to the first embodiment.

The processor 3A includes a selector 31, an image adding section 32, an image processing section 33, a driving signal generation section 34, a control section 35, and a clock signal generation section 36.

The clock signal generation section 36 is configured to generate a clock signal for synchronizing the operations in the CMOS image sensor 11 and the light source control section 21 with each other, and output the generated clock signal to the light source control section 21 and the driving signal generation section 34.

As shown in FIGS. 11 and 12, the light source control section 21 according to the present embodiment is configured to generate a light emission control signal based on the timing at which the clock signal is inputted from the clock signal generation section 36, and output the generated light emission control signal to the LED unit 22, the selector 321, and the selector 327.

In addition, as shown in FIGS. 11 and 12, the driving signal generation section 34 according to the present embodiment is configured to generate a readout start signal based on the timing at which the clock signal is inputted from the clock signal generation section 36, and output the generated readout start signal to the TG 113, the selector 321, and the selector 327.

That is, with the image pickup system 103 according to the present embodiment, the driving signal generation section 34 and the clock signal generation section 36 include a function as a trigger signal output section, and the readout start signal outputted from the driving signal generation section 34 and the clock signal outputted from the clock signal generation section 36 have a function as a trigger signal.

Next, working of the image pickup system 103 including the configuration as described above will be described.

The user turns on power sources of the respective sections of the image pickup system 103, and thereafter operates the mode switching switch 12 to give an instruction for setting the observation mode of the image pickup system 103 to the white light observation mode.

The control section 35, based on the instruction given through the mode switching switch 12, generates a system control signal for setting the observation mode of the image pickup system 103 to the white light observation mode and outputs the generated system control signal to the light source control section 21, the selector 31, and the image processing section 33.

On the other hand, the clock signal generation section 36 is configured to generate a clock signal for synchronizing the operations in the CMOS image sensor 11 and the light source control section 21 with each other, and output the generated clock signal to the light source control section 21 and the signal generation section 34.

The driving signal generation section 34 generates, once in each period T corresponding to the frame rate related to image obtainment, a readout start signal representing the timing for starting the readout of the line L1 of the light-receiving section 111, based on the timing at which the clock signal is inputted from the clock signal generation section 36, and outputs the generated readout start signal to the TG 113, the selector 321, and the selector 327.

The TG 113, based on the readout start signal outputted once in each period T from the driving signal generation section 34, matches the exposure period of each line with the period T and generates an image pickup control signal for completing the exposure of the line L1 and starting the readout of the line L1 at a timing substantially immediately after the start of the exposure of the line LN, to output the generated image pickup control signal to the light-receiving section 111.

On the other hand, the light source control section 21, when detecting that the observation mode of the image pickup system 103 is set to the white light observation mode based on the system control signal outputted from the control section 35, generates a light emission control signal for causing the respective LEDs which belong to the white-light LED group 221 to simultaneously and continuously emit light and causing the respective LEDs which belong to the special-light LED group 222 to stop light emission and outputs the generated light emission control signal to the LED unit 22. Then, in response to the output of such a light emission control signal, the white light emitted from the white-light LED group 221 is supplied to the light guide 5, and further, the object is illuminated with the white light applied through the light guide 5.

The light-receiving section 111 performs image pickup operation using the rolling-shutter method based on the image pickup control signal outputted from the TG 113, and thereby receives return light of the white light applied to the object, to generate an electric signal corresponding to the received return light and output the generated electric signal.

The signal processing section 112 generates image data by performing signal processing such as A/D conversion processing on the electric signal outputted from the light-receiving section 111, and outputs the generated image data to the selector 31.

The selector 31 operates so as to output the image data outputted from the signal processing section 112 to the image processing section 33, based on the system control signal outputted from the control section 35.

The image processing section 33, based on the system control signal outputted from the control section 35, performs image processing corresponding to the white light observation mode on the image data outputted from the selector 31, to thereby generate a video signal and output the generated video signal to the monitor 4. Specifically, the image processing section 33 performs processing such as white balance adjustment and gain adjustment on the image data outputted from the selector 31, for example, to thereby generate a video signal and output the generated video signal to the monitor 4.

On the other hand, the user operates the insertion portion of the endoscope 1 while checking the observation image displayed on the monitor 4 in the white light observation mode, and places the distal end portion of the insertion portion at a position where an image of a desired object in the body cavity can be picked up. The user then operates the mode switching switch 12 in the state where the distal end portion of the insertion portion is arranged as described, to thereby give an instruction for setting the observation mode of the image pickup system 103 to the special light observation mode.

The control section 35, based on the instruction given through the mode switching switch 12, generates a system control signal for setting the observation mode of the image pickup system 103 to the special light observation mode and outputs the generated system control signal to the light source control section 21, the selector 31, and the image processing section 33.

Figure 13:
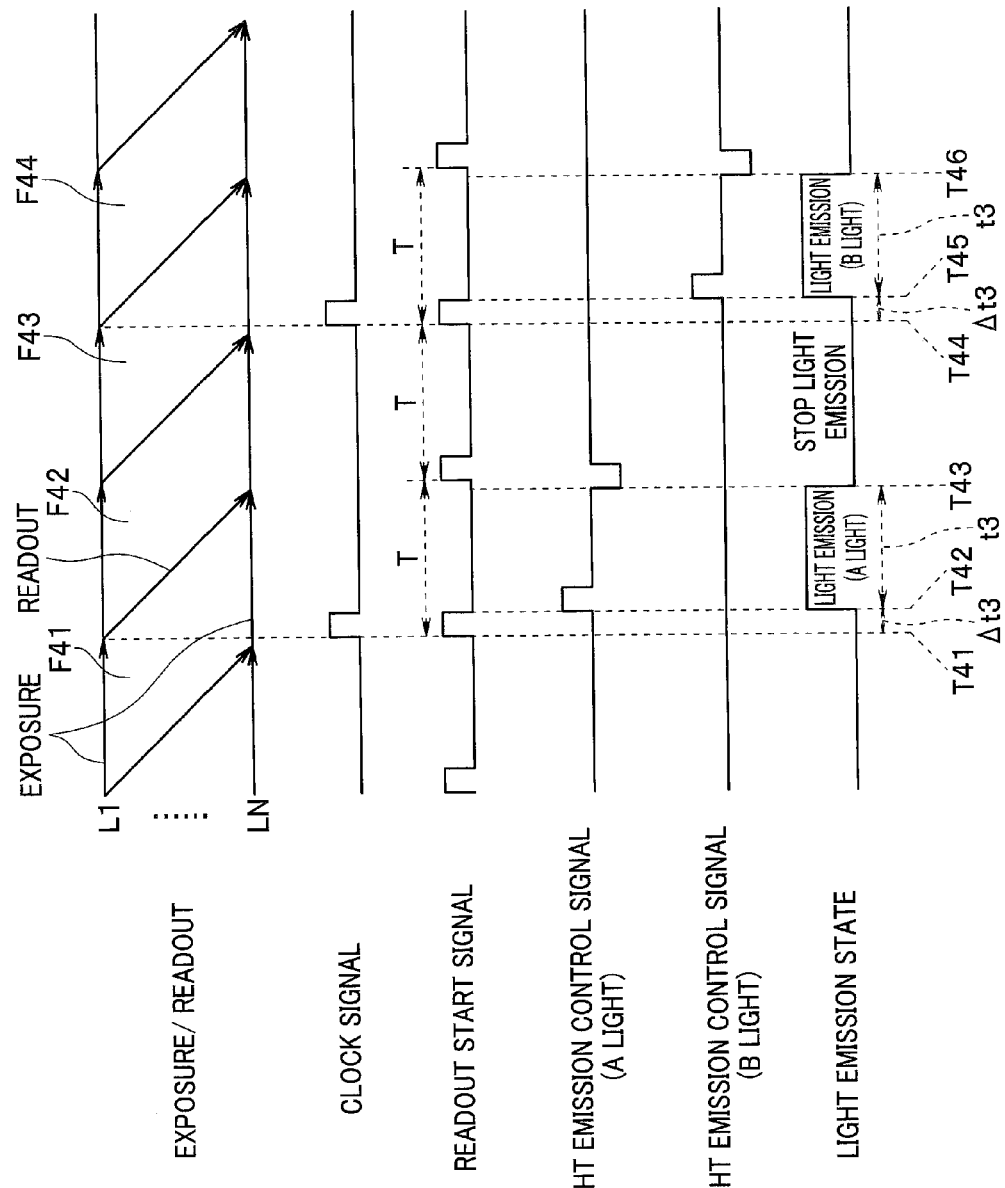
FIG. 13 describes an operation performed in the image pickup system according to the third embodiment.

Now, description will be made on the specific operation performed when the image pickup system 103 is set to the special light observation mode. FIG. 13 describes an operation performed in the image pickup system according to the third embodiment.

The TG 113, based on the readout start signal outputted once in each period T from the driving signal generation section 34, generates an image pickup control signal for completing exposure of the line L1 in a frame F41 and starting readout of the line L1 in the frame F41 at a time T41 corresponding to a timing substantially immediately after the start of exposure of the line LN in the frame F41, and outputs the generated image pickup control signal to the light-receiving section 111.

The light source control section 21 generates a light emission control signal for starting the emission of the A light by the first LED in the special-light LED group 222 at a time T42 corresponding to the timing after a delay period $\Delta t3$ has elapsed from the time T41 at which the clock signal was inputted from the clock signal generation section 36, and for terminating the emission of the A light by the first LED in the special-light LED group 222 at a time T43 corresponding to the timing after a light emission period t3 has elapsed from the time T42, and outputs the generated light emission control signal to the LED unit 22 and the image adding section 32.

The light source control section 21, when generating the above-described light emission control signal, sets the light emission period t3 so as to include the time T43 in the period after the readout of the line L1 of the light-receiving section 111 has been completed for the frame F41 until before the readout of the line L1 is started for a frame F42 (for example, immediately before the readout of the line L1 is started for the frame F42). In addition, when generating the above-described light emission control signal, the light source control section 21 sets the delay period $\Delta t3$ such that the relation of $\Delta t3 < T-t3$ is established, that is, the delay period $\Delta t3$ is smaller than the difference between the exposure period T of the line L1 in the frame F41 and the light emission period t3 of the first LED.

In response to the output of the above-described light emission control signal, in the light emission period t3 bridging over the two frames, i.e., the frames F41 and F42, the A light emitted from (the first LED in) the special-light LED group 222 is supplied to the light guide 5, and further, the object is illuminated with the A light applied through the light guide 5.

The light-receiving section 111 performs image pickup operation using the rolling-shutter method based on the image pickup control signal outputted from the TG 113, to thereby receive the return light of the A light applied to the object in the light emission period t3, and generates an electric signal corresponding to the received return light, to output the generated electric signal.

The signal processing section 112 performs signal processing such as A/D conversion processing on the electric signal outputted from the light-receiving section 111, to sequentially generate image data for the two frames F41 and F42 and output the generated image data for the two frames to the selector 31.

The selector 31 operates so as to output the image data outputted from the signal processing section 112 to the image adding section 32, based on the system control signal outputted from the control section 35.

The selector 321, based on the light emission control signal outputted from the light source control section 21 and the readout start signal outputted from the driving signal generation section 34, recognizes the image data inputted first after the start of the emission of the A light by the first LED in the special-light LED group 222, as the image data for the frame F41, and causes the memory 322 to store the image data for the frame F41. In addition, based on the light emission control signal outputted from the light source control section 21 and the readout start signal outputted from the driving signal generation section 34, the selector 321 recognizes the image data inputted secondly after the start of the emission of the A light by the first LED in the special-light LED group 222, as the image data for the frame F42, and causes the memory 323 to store the image data for the frame F42.

Based on the light emission control signal outputted from the light source control section 21 and the readout start signal outputted from the driving signal generation section 34, when the selector 327 detects that the image data for the frame F41 obtained following the emission of the A light is stored in the memory 322 and the image data for the frame F42 obtained following the emission of the A light is stored in the memory 323, the selector 327 simultaneously outputs the image data for the frames F41 and F42 to the adding circuit 328.

The adding circuit 328 performs adding processing on the image data for the frames F41 and F42 which are simultaneously outputted from the selector 327, and outputs the image data subjected to the adding processing to the image processing section 33.

On the other hand, the TG 113, based on the readout start signal outputted once in each period T from the driving signal generation section 34, generates an image pickup control signal for completing exposure of the line L1 in a frame F43 and starting readout of the line L1 in the frame F43 at a time T44 corresponding to a timing substantially immediately after the start of exposure of the line LN in the frame F43, and outputs the generated image pickup control signal to the light-receiving section 111.

The light source control section 21 generates a light emission control signal for starting the emission of the B light by the second LED in the special-light LED group 222 at a time T45 corresponding to the timing after a delay period $\Delta t3$ has elapsed from the time T44 at which the clock signal was inputted from the clock signal generation section 36, and for terminating the emission of the B light by the second LED in the special-light LED group 222 at a time T46 corresponding to the timing after a light emission period t3 has elapsed from the time T45, and outputs the generated light emission control signal to the LED unit 22 and the image adding section 32.

The light source control section 21, when generating the above-described light emission control signal, sets the light emission period t3 so as to include the time T46 in the period after the readout of the line L1 of the light-receiving section 111 has been completed for the frame F43 until before the readout of the line L1 is started for a frame F44 (for example, immediately before the readout of the line L1 is started for the frame F44). In addition, when generating the above-described light emission control signal, the light source control section 21 sets the delay period $\Delta t3$ such that the relation of $\Delta t3 < T - t3$ is established, that is, the delay period $\Delta t3$ is smaller than the difference between the exposure period T of the line L1 in the frame F43 and the light emission period t3 of the second LED.

In response to the output of the above-described light emission control signal, in the light emission period t3 bridging over the two frames, i.e., the frames F43 and F44, the B light emitted from (the second LED in) the special-light LED group 222 is supplied to the light guide 5, and further, the object is illuminated with the B light applied through the light guide 5.

The light-receiving section 111 performs image pickup operation using the rolling-shutter method based on the image pickup control signal outputted from the TG 113, to thereby receive the return light of the B light applied to the object in the light emission period t3, and generates an electric signal corresponding to the received return light, to output the generated electric signal.

The signal processing section 112 performs signal processing such as A/D conversion processing on the electric signal outputted from the light-receiving section 111, to sequentially generate image data for the two frames F43 and F44 and output the generated image data for the two frames to the selector 31.

The selector 31 operates so as to output the image data outputted from the signal processing section 112 to the image adding section 32, based on the system control signal outputted from the control section 35.

The selector 321, based on the light emission control signal outputted from the light source control section 21 and the readout start signal outputted from the driving signal generation section 34, recognizes the image data inputted first after the start of the emission of the B light by the second LED in the special-light LED group 222, as the image data for the frame F43, and causes the memory 324 to store the image data for the frame F43. In addition, based on the light emission control signal outputted from the light source control section 21 and the readout start signal outputted from the driving signal generation section 34, the selector 321 recognizes the image data inputted secondly after the start of the emission of the B light by the second LED in the special-light LED group 222, as the image data for the frame F44, and causes the memory 325 to store the image data for the frame F44.

Based on the light emission control signal outputted from the light source control section 21 and the readout start signal outputted from the driving signal generation section 34, when the selector 327 detects that the image data for the frame F43 obtained following the emission of the B light is stored in the memory 324 and the image data for the frame F44 obtained following the emission of the B light is stored in the memory 325, the selector 327 simultaneously outputs the image data for the frames F43 and F44 to the adding circuit 329.

The adding circuit 329 performs adding processing on the image data for the frames F43 and F44 which are simultaneously outputted from the selector 327, and outputs the image data subjected to the adding processing to the image processing section 33.

The image processing section 33, based on the system control signal outputted from the control section 35, performs image processing corresponding to the special light observation mode on the two image data outputted from the adding circuits 328 and 329, to thereby generate a video signal and output the generated video signal to the monitor 4. Specifically, the image processing section 33 synthesizes the two image data outputted from the adding circuits 328 and 329, for example, and performs processing such as white balance adjustment and gain adjustment on the synthesized image data, to thereby generate a video signal and output the generated video signal to the monitor 4.

As described above, the image pickup system 103 according to the present embodiment is configured to perform processing for adding and synthesizing the images for the two frames (the frames F41 and F42) obtained following the emission of the A light and processing for adding and synthesizing the images for the two frames (for the frames F43 and F44) obtained following the emission of the B light, while performing the image pickup operation using the rolling-shutter method in the special light observation mode. Therefore, the image pickup system 103 of the present embodiment is capable of suppressing the brightness unevenness of an image caused by the image pickup operation using the rolling-shutter method employed in the (light-receiving section 111 of) the CMOS image sensor 11.

In addition, the image pickup system 103 according to the present embodiment is capable of displaying an observation image having no brightness unevenness on the monitor 4, without a need for performing complicated control of changing the operation method of the CMOS image sensor 11 in accordance with the switching of the observation mode, for example.

In addition, according to the image pickup system 103 of the present embodiment, the above-described control is performed in the light source control section 21, thereby enabling the object to be irradiated with the A light and the B light at the timing at which the number of adding frames, which is required when an observation image having no brightness unevenness (and color mixture) is generated and displayed on the monitor 4, is minimized. That is, according to the image pickup system 103 of the present embodiment, the above-described control is performed in the light source control section 21, thereby capable of minimizing, as much as possible, a decrease in the frame rate when an observation image having no brightness unevenness and color mixture is generated and displayed on the monitor 4.

Figure 14:
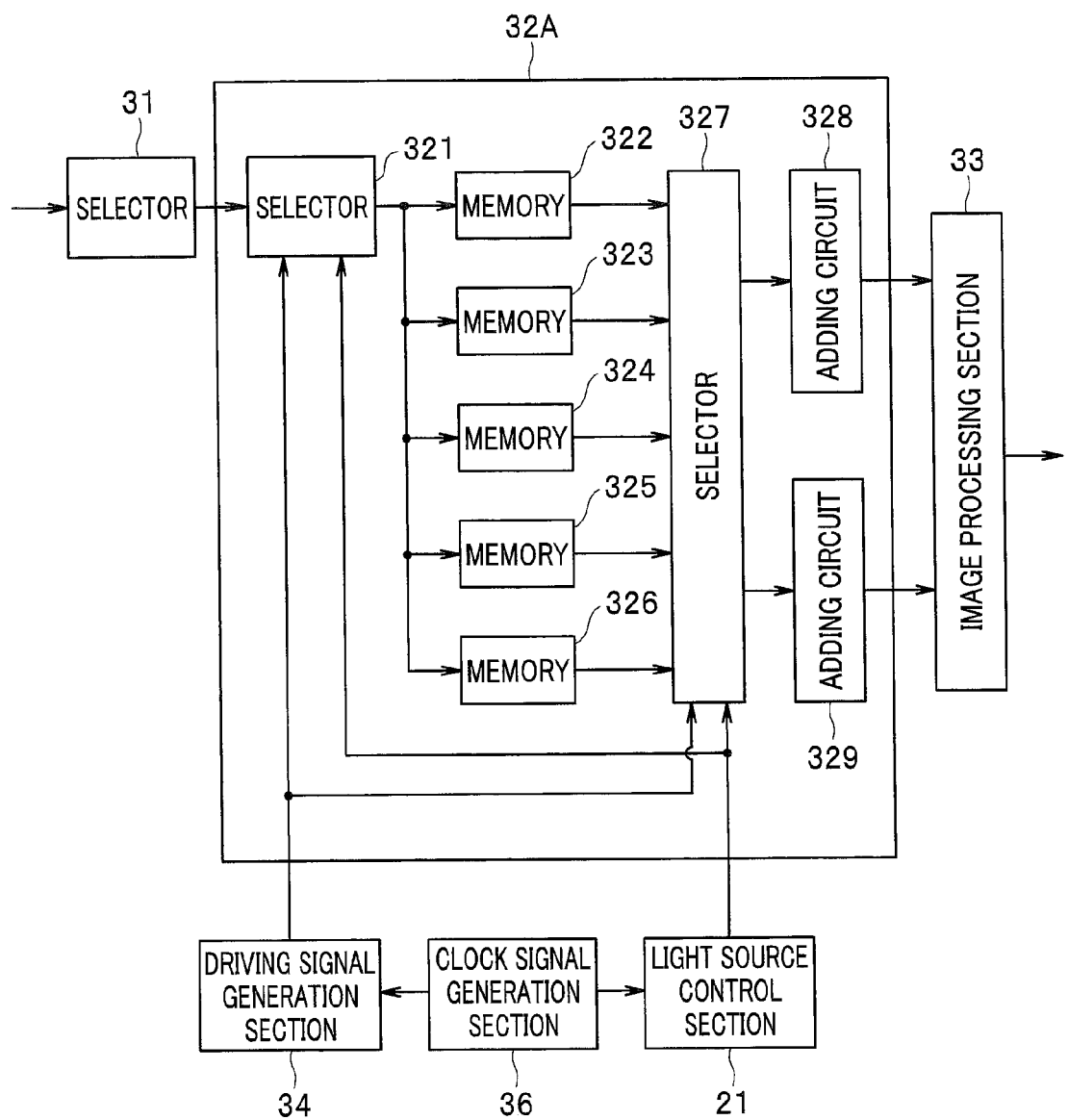
FIG. 14 is a block diagram showing an example of a specific configuration of an image adding section according to a modified example of the third embodiment.

Note that, according to the present embodiment, when the emission period of the A light is required to be sufficiently longer than the emission period of the B light in order to adjust the color balance of the observation image displayed on the monitor 4, for example, the image pickup system 103 may be configured by using an image adding section 32A exemplified in FIG. 14, instead of the image adding section 32 exemplified in FIG. 12. FIG. 14 is a block diagram showing an example of a specific configuration of an image adding section according to a modified example of the third embodiment.

Figure 15:
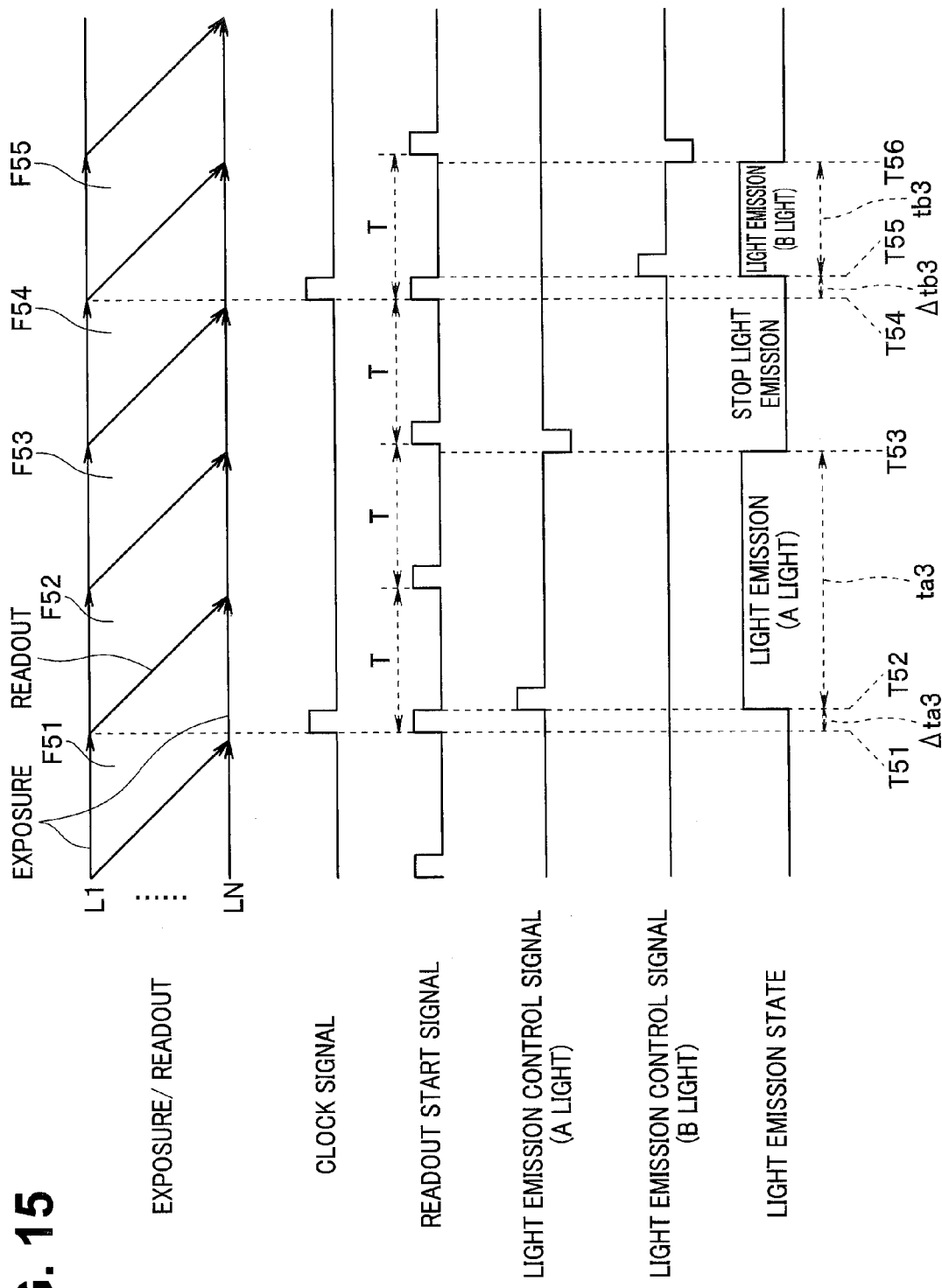
FIG. 15 describes an operation performed in the image pickup system according to the modified example of the third embodiment.

Now description will be made on the specific operation performed when the image pickup system 103 provided with the image adding section 32A is set to the special light observation mode. FIG. 15 describes an operation performed in the image pickup system according to the modified example of the third embodiment. Note that, hereinafter description will be made by taking a case where the emission period of the A light is longer than the exposure period T for one frame and shorter than the exposure period 2T for two frames, as an example.

The TG 113, based on the readout start signal outputted once in each period T from the driving signal generation section 34, generates an image pickup control signal for completing exposure of the line L1 in a frame F51 and starting readout of the line L1 in the frame F51 at a time T51 corresponding to a timing substantially immediately after the start of exposure of the line LN in the frame F51, and outputs the generated image pickup control signal to the light-receiving section 111.

The light source control section 21 generates a light emission control signal for starting the emission of the A light by the first LED in the special-light LED group 222 at a time T52 corresponding to the timing after a delay period $\Delta ta3$ has elapsed from the time T51 at which the clock signal was inputted from the clock signal generation section 36, and for terminating the emission of the A light by the first LED in the special-light LED group 222 at a time T53 corresponding to the timing after a light emission period ta3 has elapsed from the time T52, and outputs the generated light emission control signal to the LED unit 22 and the image adding section 32.

The light source control section 21, when generating the above-described light emission control signal, sets the light emission period ta3 so as to include the time T53 in the period after the readout of the line L1 of the light-receiving section 111 has been completed for a frame F52 until before the readout of the line L1 is started for a frame F53 (for example, immediately before the readout of the line L1 is started for the frame F53). In addition, when generating the above-described light emission control signal, the light source control section 21 sets the delay period $\Delta ta3$ such that the relation of $\Delta ta3<2T-ta3$ is established, that is, the delay period $\Delta ta3$ is smaller than the difference between the period obtained by doubling the exposure period T of the line L1 in the frame F51 and the light emission period ta3 of the first LED.

In response to the output of the above-described light emission control signal, in the light emission period ta3 bridging over the three frames, i.e., the frames F51, F52 and F53, the A light emitted from (the first LED in) the special-light LED group 222 is supplied to the light guide 5, and further, the object is illuminated with the A light applied through the light guide 5.

The light-receiving section 111 performs image pickup operation using the rolling-shutter method based on the image pickup control signal outputted from the TG 113, to thereby receive the return light of the A light applied to the object in the light emission period ta3, and generates an electric signal corresponding to the received return light, to output the generated electric signal.

The signal processing section 112 performs signal processing such as A/D conversion processing on the electric signal outputted from the light-receiving section 111, to sequentially generate image data for the three frames F51, F52 and F53 and output the generated image data for the three frames to the selector 31.

The selector 31 operates so as to output the image data outputted from the signal processing section 112 to the image adding section 32, based on the system control signal outputted from the control section 35.

The selector 321, based on the light emission control signal outputted from the light source control section 21 and the readout start signal outputted from the driving signal generation section 34, recognizes the image data inputted first after the start of the emission of the A light by the first LED in the special-light LED group 222, as the image data for the frame F51, and causes the memory 322 to store the image data for the frame F51. In addition, based on the light emission control signal outputted from the light source control section 21 and the readout start signal outputted from the driving signal generation section 34, the selector 321 recognizes the image data inputted secondly after the start of the emission of the A light by the first LED in the special-light LED group 222, as the image data for the frame F52, and causes the memory 323 to store the image data for the frame F52. In addition, based on the light emission control signal outputted from the light source control section 21 and the readout start signal outputted from the driving signal generation section 34, the selector 321 recognizes the image data inputted thirdly after the start of the emission of the A light by the first LED in the special-light LED group 222, as the image data for the frame F53, and causes the memory 324 to store the image data for the frame F53.

Based on the light emission control signal outputted from the light source control section 21 and the readout start signal outputted from the driving signal generation section 34, when the selector 327 detects that the image data for the frame F51 obtained following the emission of the A light is stored in the memory 322, the image data for the frame F52 obtained following the emission of the A light is stored in the memory 323, and the image data for the frame F53 obtained following the emission of the A light is stored in the memory 324, the selector 327 simultaneously outputs the image data for the frames F51, F52, and F53 to the adding circuit 328.

The adding circuit 328 performs adding processing on the image data for the frames F51, F52, and F53 which are simultaneously outputted from the selector 327, and outputs the image data subjected to the adding processing to the image processing section 33.

On the other hand, the TG 113, based on the readout start signal outputted once in each period T from the driving signal generation section 34, generates an image pickup control signal for completing exposure of the line L1 in a frame F54 and starting readout of the line L1 in the frame F54 at a time T54 corresponding to a timing substantially immediately after the start of exposure of the line LN in the frame F54, and outputs the generated image pickup control signal to the light-receiving section 111.

The light source control section 21 generates a light emission control signal for starting the emission of the B light by the second LED in the special-light LED group 222 at a time T55 corresponding to the timing after a delay period $\Delta tb3$ has elapsed from the time T54 at which the clock signal was inputted from the clock signal generation section 36, and for terminating the emission of the B light by the second LED in the special-light LED group 222 at a time T56 corresponding to the timing after a light emission period tb3 has elapsed from the time T55, and outputs the generated light emission control signal to the LED unit 22 and the image adding section 32.

The light source control section 21, when generating the above-described light emission control signal, sets the light emission period tb3 so as to include the time T56 in the period after the readout of the line L1 of the light-receiving section 111 has been completed for the frame F54 until before the readout of the line L1 is started for a frame F55 (for example, immediately before the readout of the line L1 is started for the frame F55). In addition, when generating the above-described light emission control signal, the light source control section 21 sets the delay period Δtb3 such that the relation of Δtb3<T−tb3 is established, that is, the delay period Δtb3 is smaller than the difference between the exposure period T of the line L1 in the frame F54 and the light emission period tb3 of the second LED.

In response to the output of the above-described light emission control signal, in the light emission period tb3 bridging over the two frames, i.e., the frames F54 and F55, the B light emitted from (the second LED in) the special-light LED group 222 is supplied to the light guide 5, and further, the object is illuminated with the B light applied through the light guide 5.

The light-receiving section 111 performs image pickup operation using the rolling-shutter method based on the image pickup control signal outputted from the TG 113, to thereby receive the return light of the B light applied to the object in the light emission period tb3, and generates an electric signal corresponding to the received return light, to output the generated electric signal.

The signal processing section 112 performs signal processing such as A/D conversion processing on the electric signal outputted from the light-receiving section 111, to sequentially generate image data for the two frames F54 and F55 and output the generated image data for the two frames to the selector 31.

The selector 31 operates so as to output the image data outputted from the signal processing section 112 to the image adding section 32, based on the system control signal outputted from the control section 35.

The selector 321, based on the light emission control signal outputted from the light source control section 21 and the readout start signal outputted from the driving signal generation section 34, recognizes the image data inputted first after the start of the emission of the B light by the second LED in the special-light LED group 222, as the image data for the frame F54, and causes the memory 325 to store the image data for the frame F54. In addition, based on the light emission control signal outputted from the light source control section 21 and the readout start signal outputted from the driving signal generation section 34, the selector 321 recognizes the image data inputted secondly after the start of the emission of the B light by the second LED in the special-light LED group 222, as the image data for the frame F55, and causes the memory 326 to store the image data for the frame F55.

Based on the light emission control signal outputted from the light source control section 21 and the readout start signal outputted from the driving signal generation section 34, when the selector 327 detects that the image data for the frame F54 obtained following the emission of the B light is stored in the memory 325 and the image data for the frame F55 obtained following the emission of the B light is stored in the memory 326, the selector 327 simultaneously outputs the image data for the frames F54 and F55 to the adding circuit 329.

The adding circuit 329 performs adding processing on the image data for the frames F54 and F55 which are simultaneously outputted from the selector 327, and outputs the image data subjected to the adding processing to the image processing section 33.

The image processing section 33, based on the system control signal outputted from the control section 35, performs image processing corresponding to the special light observation mode on the two image data outputted from the adding circuits 328 and 329, to thereby generate a video signal and output the generated video signal to the monitor 4. Specifically, the image processing section 33 synthesizes the two image data outputted from the adding circuits 328 and 329, for example, and performs processing such as white balance adjustment and gain adjustment on the synthesized image data, to thereby generate a video signal and output the generated video signal to the monitor 4.

As described above, the image pickup system 103 according to the present modified example is configured to perform processing for adding and synthesizing the images for the three frames (the frames F51, F52, and F53) obtained following the emission of the A light and processing for adding and synthesizing the images for the two frames (the frames F54 and F55) obtained following the emission of the B light, while performing image pickup operation using the rolling-shutter method in the special light observation mode. Therefore, the image pickup system 103 of the present modified example is capable of suppressing the brightness unevenness of an image caused by the image pickup operation using the rolling-shutter method employed in the (light-receiving section 111 of) the CMOS image sensor 11.

Note that, according to the above-described embodiments, the image pickup system is not limited to a configuration in which the special-light LED group 222 is controlled so as to continuously emit light in the light emission period in the special light observation mode, but may be configured such that the special-light LED group 222 is controlled so as to emit pulse light, the number of light emission and/or pulse width of which is adjusted so as to match the light emission period, for example.

In addition, according to the above-described embodiments, the image pickup system is not limited to the one having a configuration in which images obtained by reading out all of the pixels of the light-receiving section 111 are added to one another in the image adding section 32, but, for example, may be configured such that adding processing is performed on an interpolation image obtained by performing interpolation processing on the image (for one frame) obtained by reading out one group of pixels including half of the all pixels of the light-receiving section 111 and an interpolation image obtained by performing interpolation processing on the image (for one frame) obtained by reading out another group of pixels including another half of all of the pixels of the light-receiving section 111, which is not included in the one group of pixels. Alternatively, according to the above-described embodiments, adding processing may be performed on an interpolation image obtained by performing interpolation processing on the image (for one frame) obtained by reading out one group of lines composed of odd-number of lines among the lines L1 to LN of the light-receiving section 111 and an interpolation image obtained by performing interpolation processing on the image (for one frame) obtained by reading out another group of lines composed of even-number of lines among the lines L1 to LN of the light-receiving section 111, in the image adding section 32, for example. Then, by adjusting the light emission period in the special light observation mode so as to adapt to such configurations, it is possible to suppress the brightness unevenness caused due to the image pickup operation using the rolling-shutter method, while improving the frame rate related to image obtainment in the CMOS image sensor 11.

It goes without saying that the present invention is not limited to the above-described embodiments, and various changes and modifications are possible without departing from the gist of the invention.

What is claimed is:

1. An image pickup system comprising:
   an image sensor configured to receive light from an object and perform an image pickup operation using a rolling-shutter method in which exposure and readout are performed in a predetermined time cycle;
   a generator configured to generate a driving signal for controlling the image sensor such that exposure and readout are performed in the image sensor in the predetermined time cycle;
   an adding section configured to add image pickup signals from an image pickup signal in a predetermined frame, which is read out from the image sensor, to an image pickup signal in an Nth frame (N is an integer equal to or larger than 2) with the predetermined frame being set as a first frame, and output the added image pickup signals;
   a light source configured to emit light for illuminating the object;
   a trigger signal output section configured to output a trigger signal which represents either a first timing at which readout of a first line in the predetermined frame is started in the image sensor or a second timing at which readout of a last line in a frame immediately before the predetermined frame has been completed in the image sensor; and
   a light source control section configured to perform control for starting light emission by the light source after an input of the trigger signal from the trigger signal output section and terminating light emission by the light source in a period after completion of readout of a first line in an N-1th frame, with the predetermined frame as a reference, until before a start of readout of a first line in the Nth frame.

2. The image pickup system according to claim 1, wherein the trigger signal output section outputs a trigger signal representing the first timing when the image sensor performs an operation for causing the readout of the first line in the predetermined frame to be started at a timing substantially immediately after a start of exposure of a last line in the predetermined frame.

3. An image pickup system according to claim 1, wherein the trigger signal output section outputs a trigger signal representing the second timing when the image sensor performs an operation for causing the readout of the first line in the predetermined frame to be started after a predetermined blank period has elapsed from a timing at which exposure of a last line in the predetermined frame has been started.

* * * * *